(12) United States Patent
Lynn

(10) Patent No.: US 11,241,149 B2
(45) Date of Patent: Feb. 8, 2022

(54) IMAGING DEVICE ATTACHMENT COMPATIBLE WITH A MOBILE DEVICE

(71) Applicant: The Regents of the University of Colorado, Denver, CO (US)

(72) Inventor: Darren D. Lynn, Denver, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 16/892,358

(22) Filed: Jun. 4, 2020

(65) Prior Publication Data

US 2020/0383559 A1 Dec. 10, 2020

Related U.S. Application Data

(60) Provisional application No. 62/857,177, filed on Jun. 4, 2019.

(51) Int. Cl.
*A61B 5/15* (2006.01)
*A61B 1/227* (2006.01)
(Continued)

(52) U.S. Cl.
CPC .......... *A61B 1/227* (2013.01); *A61B 1/00195* (2013.01); *A61B 1/00197* (2013.01);
(Continued)

(58) Field of Classification Search
CPC . A61B 1/227; A61B 1/00195; A61B 1/00197; A61B 1/04; A61B 1/00108;
(Continued)

(56) References Cited

U.S. PATENT DOCUMENTS 4,685,452 A * 8/1987 Riester ............... A61B 1/07
600/200
7,137,948 B2 * 11/2006 Tsai ................... A61B 1/00052
600/109

(Continued)

FOREIGN PATENT DOCUMENTS

CA 2941213 A1 7/2008

OTHER PUBLICATIONS

Pacific Northwest National Laboratory, "PNNL Smartphone Microscope," https://availabletechnologies.pnnl.gov/technology.asp?id=393, 2 pages, Jun. 2020.
(Continued)

*Primary Examiner* — Howard D Brown, Jr.

(57) ABSTRACT

An enhanced optical design for imaging of live human tissue as a supplemental attachment to wireless mobile devices such as smartphones. The improved imaging system includes a series of optical ball lenses coupled to a medical-grade light source to allow universal compatibility to mobile device (e.g., smartphone) cameras. The releasable optical attachment comprises optical enhancement elements allowing universal compatibility without the need of an application or special program to re-orient the image therein permitting less loss of picture acuity and blanket usability to HIPAA-verified smartphone applications used in hospitals and patient's electronic health records. The addition of an external light source and light-redirecting elements negates the need for a smartphone light source or smartphone re-programming to illuminate target.

20 Claims, 33 Drawing Sheets

(51) Int. Cl.
*H04M 1/02* (2006.01)
*H04N 5/225* (2006.01)
*A61B 1/00* (2006.01)
*A61B 1/04* (2006.01)

(52) U.S. Cl.
CPC ............ *A61B 1/04* (2013.01); *H04M 1/0264* (2013.01); *H04N 5/2254* (2013.01); *H04M 2250/52* (2013.01); *H04N 2005/2255* (2013.01)

(58) Field of Classification Search
CPC .. H04M 1/0264; H04M 2250/52; H04M 1/21; H04N 5/2254; H04N 2005/2255; H04N 5/2256
See application file for complete search history.

(56) References Cited

U.S. PATENT DOCUMENTS

| | | | | |
|---|---|---|---|---|
| 7,399,275 | B2* | 7/2008 | Goldfain | A61B 1/00188 600/112 |
| 8,066,634 | B2* | 11/2011 | Andreassen | A61B 1/227 600/200 |
| 9,241,663 | B2* | 1/2016 | Jena | A61B 5/150358 |
| 10,436,773 | B2* | 10/2019 | Depa | G01N 33/521 |
| 2010/0210929 | A1* | 8/2010 | Jossart | A61B 5/6838 600/323 |
| 2011/0200287 | A1* | 8/2011 | Pfnuer | G02B 7/027 385/93 |
| 2011/0240886 | A1* | 10/2011 | Tokhtuev | G01N 21/645 250/461.1 |
| 2015/0065803 | A1 | 3/2015 | Douglas et al. | |
| 2017/0071509 | A1* | 3/2017 | Pandey | A61B 5/14546 |
| 2019/0216307 | A1* | 7/2019 | Coon | A61B 3/0091 |
| 2020/0029837 | A1* | 1/2020 | Joudi | A61B 1/227 |
| 2020/0297204 | A1* | 9/2020 | Vivenzio | A61B 1/06 |
| 2020/0384287 | A1* | 12/2020 | Hetz | A61N 5/0616 |
| 2021/0117385 | A1* | 4/2021 | Haldar | G06F 16/128 |

OTHER PUBLICATIONS

Wallace, John, "UC Davis Researchers Prove That iPhone Plus Ball Lens Equals Useful Microscope," LaserFocus World, https://www.laserfocusworld.com/test-measurement/spectroscopy/article/16562721/uc-davis-researchers-prove-that-iphone-plus-ball-lens-equals-useful-microscope, 10 pages, Oct. 6, 2011.

Bhavana, Kranti et al., "Smartphone Otoscopy Sans Attachment: A Paradigm Shift In Diagnosing Ear Pathologies," American Academy of Otolaryngology—Head and Neck Surgery, 6 pages, Jun. 12, 2018.

* cited by examiner

SECTION C-C

SECTION A-A

SECTION B-B

SECTION A-A

SECTION B-B

SECTION B-B

SECTION C-C

IMAGING DEVICE ATTACHMENT COMPATIBLE WITH A MOBILE DEVICE

CROSS REFERENCE TO RELATED APPLICATIONS

This application claims priority to U.S. Provisional Application Ser. No. 62/857,177 filed Jun. 4, 2019, which is incorporated herein by reference in its entirety for all purposes.

TECHNICAL FIELD

Various embodiments of the present technology generally relate to devices and methods for directing and focusing light to an imaging device for obtaining images of human tissue. More specifically, some embodiments relate more particularly to devices, systems, and methods for utilizing smartphone cameras as an otoscope for examination of the anatomy of the human ear.

BACKGROUND

Telemedicine has increased in importance to clinicians in a number of medical practice areas, and for both specialists and general practitioners. Increasing imaging capabilities and communication speeds of smartphones have facilitated provision of new tools for diagnosing conditions remotely. For example, acute otitis media (AOM) is one of the most common diseases of childhood. It is estimated that 75% of children have at least one episode of AOM before their first birthday. This leads to physician visits for about 1.8 million Canadian children younger than 5 years old annually and is the primary condition for which antibacterial agents were prescribed to children in the United States in 2006.

Numerous studies conducted over the past fifteen years have shown that both trainees and practitioners have suboptimal ability to diagnoses the presence of middle-ear effusion. Many reasons could explain why ear examination in children is so challenging such as difficulty in child immobilization leading to a short period of time for otoscopy, commonly seen redness of the eardrum caused by crying or fever, parental anxiety toward ear examination, presence of cerumen precluding visualization of the entire tympanic membrane and small or angulated external auditory canal, especially in young children. As technology takes on an increasingly central role in medicine, devices such as video laryngoscopes and portable ultrasounds are now widely used.

At least some known attachments for providing smartphone-compatible otoscopes allow practitioners the ability to obtain diagnostic-quality video and images using a portable platform. Such devices may be compact enough to fit in a pocket and they employ the imaging and lighting capabilities of the smartphone to capture reproducible images of the external ear canal and tympanic membrane. These known devices may be used for tele-otoscopy and enable parents to record their children's ear examinations and send the images or video for remote diagnosis by medical practitioners.

Known devices, systems and methods for tele-otoscopy using smartphones may rely on the native smartphone camera light source, and may require the target image to be virtually inverted with an app in both the horizontal and vertical planes. Furthermore, known devices for attaching otoscopes to smartphones may be designed for use with specific phone models. Similarly, the optics and other design considerations of such known otoscope attachments for smartphones may need to be specifically designed according to the specifications of the native smartphone light source. Just as the shapes and sizes of the numerous smartphones available on the market vary widely, so too do the light source specifications, thereby limiting the adoption of tele-otoscopy for known smartphone otoscope attachments. Known devices, systems and methods for tele-otoscopy using smartphones may thus be impractical for both medical practices and patients, as well as manufacturers and suppliers, who may need to obtain, use, or supply customized attachments for the multitude of smartphone models. Furthermore, a lack of universal fit of known tele-otoscopy devices and systems to numerous different smartphone models presents inconvenience and inefficiency in the common case of providers, patients, and caregivers obtaining new phones for day-to-day use.

Accordingly, a need exists for technology that overcomes the problems demonstrated above, as well as one that provides additional benefits. The examples provided herein of some prior or related systems and their associated limitations are intended to be illustrative and not exclusive. Other limitations of existing or prior systems will become apparent to those of skill in the art upon reading the following Detailed Description.

DRAWINGS

Embodiments of the present technology will be described and explained through the use of the accompanying drawings.

Figure 1A:
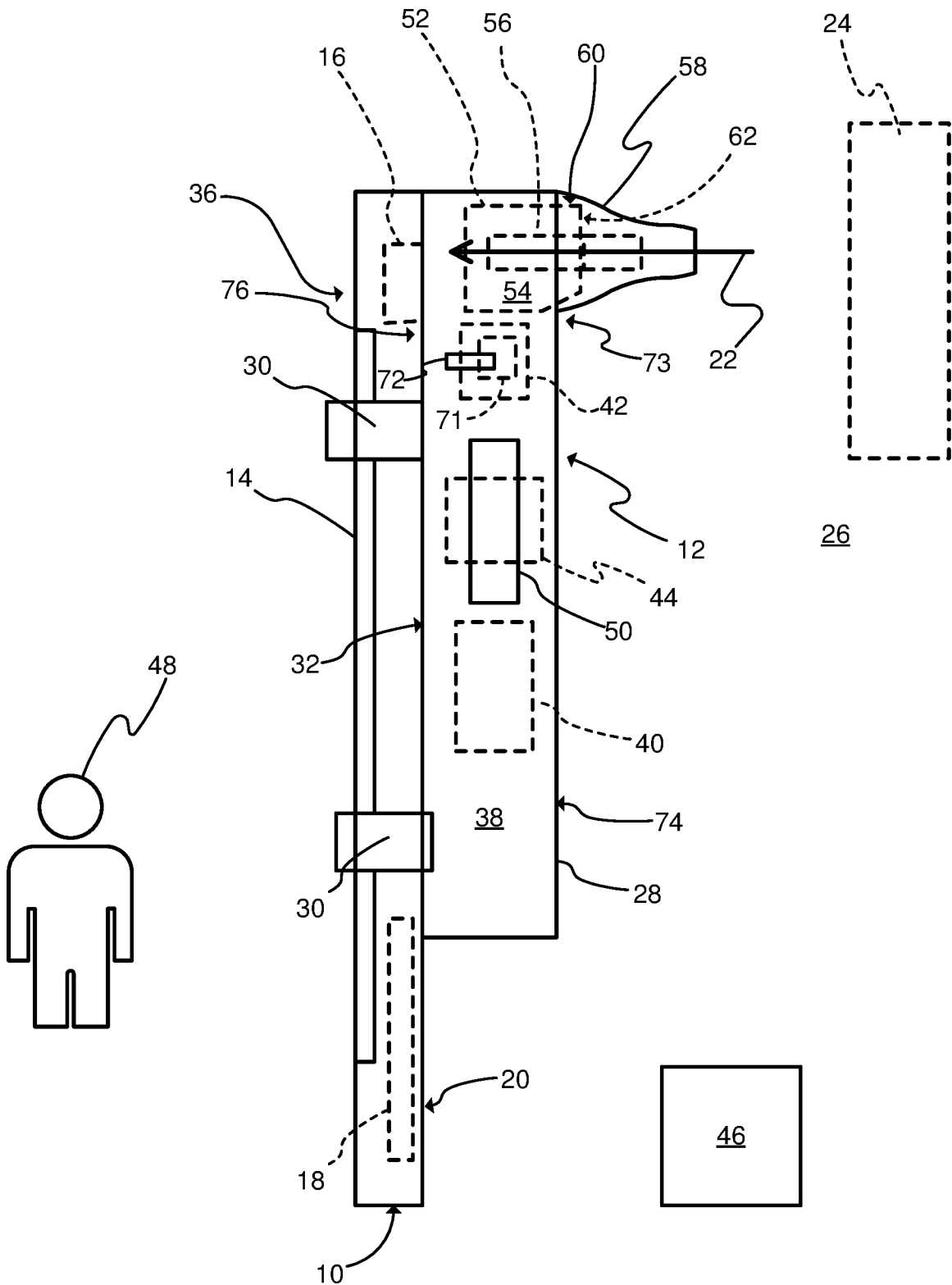
FIGS. 1A-1C depict side, front and perspective views of a smartphone with a mobile imaging device attachment, according to an embodiment of the present technology.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

A mobile imaging device attachment according to the present technology can be used with mobile devices like smartphones to image human tissue. In some embodiments, the mobile imaging device attachment can be an otoscope or auriscope attachment for coupling to a mobile device. The otoscope attachment can be used to look into a person's ears and inspect tissue such as the tympanic membrane.

In some implementations, the mobile device is a smartphone such as those that operate using the iOS or Android operating system. The mobile imaging device attachment can be coupled to the smartphone and used to image human tissue such as the tympanic membrane.

The combination of the otoscope attachment and the smartphone can form an otoscope or auriscope, which is a medical device that is used to look into the ears. The otoscope can be used by health care providers to screen for illness during regular check-ups and investigate ear symptoms. It can also be used by parents and other non-providers to provide images and video for purposes such as remote diagnosis, telemedicine, and the like.

The otoscope gives a view of the ear canal and tympanic membrane or eardrum. Because the eardrum is the border separating the external ear canal from the middle ear, its characteristics can be indicative of various diseases of the middle ear space.

The smartphone otoscope attachment assembly of the present technology can include a body and a head. The attachment can include a light source and one or more lenses, such as ball lenses, that provide an image to the camera of the smartphone. The distal (e.g., front) end of the smartphone otoscope attachment assembly can include a means for attaching an ear specula. The ear specula may be disposable and made of plastic.

The otoscope attachment assembly of the present technology can be used in a variety of ways. In some embodiments, a user can attach the assembly to the back of a smartphone such as an iPhone so that the lens array is aligned with the aperture of the smartphone camera. The user can activate the light source of the assembly by pushing a button or using other suitable means. The light source can be powered by one or more batteries positioned in the body of the otoscope attachment assembly.

Similar to how traditional otoscopes are used, the user can straighten the ear canal of the human subject of the examination by pulling on the pinna (usually the earlobe, side or top of the ear) and then insert the ear speculum side of the otoscope attachment assembly into the external ear. The user can then see the inside of the ear canal on the smartphone's display.

The smartphone otoscope attachment assembly of the present technology can be embodied in numerous design configurations. In one embodiment, the otoscope attachment assembly can be mountable on a wall, tripod, or other supportive structure. In other embodiments, the otoscope attachment assembly is portable. A wall-mounted otoscope attachment assembly can be attached to a base with a flexible power cord, which serves to hold the otoscope attachment when it is not in use and also serves as a source of electric power when plugged into an electric outlet. Portable configurations of the present technology can be powered by at least one battery position in the assembly body. In one embodiment, the one or more batteries are rechargeable battery cell(s) and the base on the otoscope attachment assembly can include a connector and accompanying electronic components for electrically coupling the cell(s) to a suitable battery charger unit.

The otoscope attachment assembly of the present technology can be used to examine the ear canal and tympanic membrane. It can also be used to examine the nose. For nose examination, a separate specialized speculum can be used or, in some embodiments, the speculum can be a dual-purpose speculum suitable for examination of both ear and nose anatomy. The assembly according to the present technology can further be used to examine the upper throat area, which can be facilitated by removal of the speculum in some embodiments.

In some embodiments, the smartphone otoscope attachment assembly of the present technology can include a speculum, a head, and a body. The speculum is the component part of the assembly that is inserted into the ear canal or other body orifice. In some embodiments, the speculum is removably coupled to the head of the assembly to facilitate use of variously shaped and dimensioned specula (e.g., lengths and diameters) to suit anatomical variations of examination subjects. The head is the component part of the assembly that contains the lens array through which light reflected from the examination area passes to the camera of the mobile device to be converted into a digital image or video. The body is the component part of the assembly to which the head is attached and that can be used to provide power to the attachment assembly by way of battery cell(s) or an external power cord (e.g., AC power). The body can be shaped and sized, and formed of a material of construction, to facilitate the assembly being held securely by the user during operation. This shape can be informed by ergonomic and other design considerations. In some embodiments, the head is removably coupled to the body to facilitate use of various design configurations of optics or light sources for different examination subjects or scenarios. For example, a first head may have a lens array providing a greater level of optical magnification as compared to a second head. Similarly, removal of the head can facilitate any needed restorative or preventative maintenance of this component for use in the assembly of the present technology.

The light source of the assembly of the present technology can be positioned in at least one of the head and the body. The light source is the component part of the assembly used to illuminate the examination area. The light source can include suitable lighting devices including, for example and without limitation, halogen, xenon, and light emitting diode (LED)-based devices and associated electronics or optical filters.

In one implementation, the speculum can be removably coupled to the head to facilitate removal and reinstallation of different specula, as desired by the user. In one embodiment, the speculum can be removably coupled to the body of the assembly by way of an interlocking tabbed interface. In the embodiment, both the speculum and the head can have a set of tabs that interlock with each other, where the speculum can be attached to the body by aligning the tabs on the speculum with corresponding spaces on the head, or vice versa. For instance, the user can push the tabs of the speculum into the corresponding spaces in the head and then rotate the speculum while holding the head stationary to secure the two components together for use, with the tabs engaging each other in an interlocking fashion. The reverse of this manual operation provides for removal of the speculum from the head by the user. In another embodiment, the speculum and the head include mating threads and the speculum can be alternately screwed onto and from the head. A snap fit or Luer-lock removably attachment can be employed in some embodiments, as can various other designs for removably coupling the speculum to the head of the assembly.

Various embodiments of the present technology provide several advantageous technical effects as compared to at least some known devices, systems and methods for providing smartphone-compatible otoscope attachments. A non-exhaustive list of such advantages of the disclosed mobile imaging device attachment is provided, as follows.

An app is not needed to flip the image. The lens array used in the smartphone otoscope attachment assembly can negate the need to re-orient the image in either the horizontal, or vertical, plane.

The lens array of the present technology can use one or more ball lenses positioned adjacent one another. Although ball lenses may, in some optical applications, distort images, the disclosed designs of the smartphone otoscope attachment assembly can enable the resulting image to be re-oriented with minimal, or no, image quality loss.

At least some known smartphone-compatible imaging devices use the native flash or flashlight of the smartphone. These native smartphone light sources can have a poor color rendering index (CRI), making it difficult for viewers of the resulting images or videos to properly see red or inflamed tissues. Moreover, since smartphone cameras may offer constant lighting in video mode, but not in still picture mode, users may be unable to utilize the imaging device unless they use a corresponding app. The embodiments of the present technology provide an external light source having a better CRI as compared to the native smartphone lighting. Users of the disclosed embodiments are thus enabled to take pictures or videos without an app and regardless of the smartphone model. Tympanic membranes and other tissues can thus be imaged and viewed using the present technology in manner that, as compared to known smartphone otoscope attachments, is more akin to how the tissue would appear using a traditional otoscope under, for example, halogen or other medical-grade light. The presence of the external light source in the otoscope attachment of the present technology, along with light-redirecting elements, negates the need for, and the variability of, native smartphone light sources or smartphone re-programming to properly, and consistently, illuminate the target tissue for examination and diagnosis.

A further advantage of these features of the present technology is that the external light source of the disclosed otoscope attachment assembly can be used as a general-purpose medical-grade light pen for examination and other clinical applications.

The attachment assemblies of the present technology need not be custom shaped and dimensioned according to specific smartphone models. The enables universal, or near universal, adaptability with the multitude of smartphone models in use by medical practitioners and patients.

The releasable optical attachment according to the present technology can include optical enhancement elements allowing universal smartphone compatibility without the need of an app or specialized software programs to re-orient the image. This provides less loss of picture acuity as well as blanket usability with HIPAA-verified smartphone applications used in hospitals and for patient's electronic health records, more generally.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Figure 1B:
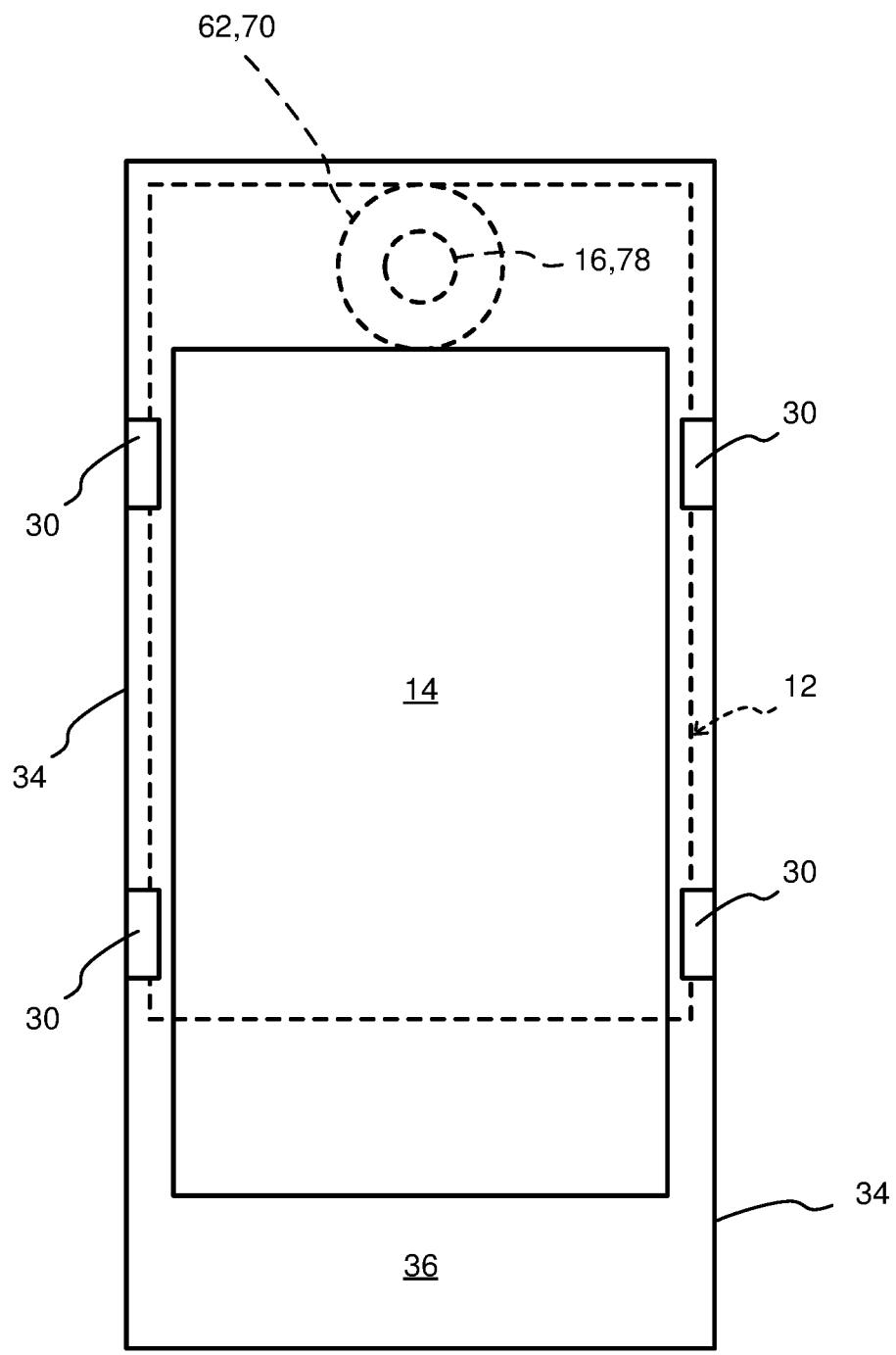

FIGS. 1A and 1B depict side and front views of a smartphone 10 with a mobile imaging device attachment 12, according to an embodiment of the present technology. Attachment 12 may also be referred to herein as an attachment assembly because, in some embodiments, attachment includes multiple, functionally related, component parts, as described herein. The smartphone 10 includes, among other components known to those having ordinary skill in the art, a display device 14, an imaging device 16 (e.g., digital camera) and analog and digital electronic components 18 including computing processors (e.g., multi-core central processing unit(s) (CPU(s)), memory storage devices, communications components, and electric power supplies (e.g., a rechargeable battery cell). The imaging device 16 is positioned with its aperture facing in the same direction as the back 20 of smartphone 10 to receive light 22 reflected from surface(s) of object(s) 24 in the exterior environment 26. Imaging device 16 includes light transducing sensors that provide input signals to the processor(s) for generating, and storing in memory, digital images or videos. These data may be transmitted from the smartphone to remote destinations via cellular networks, the Internet, wired (e.g., serial) connections, among other methods.

The mobile imaging device attachment 12 shown in FIGS. 1A and 1B can include a body 28. In some embodiments, the body 28 is formed, at least in part, as a one-piece construction from suitable lightweight materials such as plastics or metals. The body 28 includes one or more means 30 for removably attaching the body 28 to the smartphone 10. In the illustrated embodiment, the attaching means 30 are clips 30 that extend from one side 32 of the body 28 for removably, yet securely, fitting over edges 34 of smartphone 10 and further extending over a portion of its front 36. In other embodiments, not shown, the attaching means 30 can include one or more magnets for removable attachment to corresponding magnetic surfaces positioned on portion(s) of the smartphone 10. Additional attaching means 30 are shown and described below with reference to additional figures. Still further attaching means 30 suitable for use with the present technology may be readily envisioned by persons having ordinary skill in the art.

Body 28 can include an at least partially hollow interior cavity 38 in which may be housed components and subsystems necessary for operation of the attachment 12 according to the present technology. Cavity 38 can house a power supply 40 (e.g., battery cell(s)), at least one light source 42, and digital or analog electronic components 44 for purposes including, for example and without limitation, transmitting electric current from power supply or source 40 to light source 42, receiving power from an external source (e.g., a charger unit 46), and receiving a manual input from a user 48 via a means 50 for adjusting a brightness, color, or other properties of light emitted by light source 42. In the illustrated embodiment, the adjusting means 50 is a dial device 50 operably coupled to one or more electronic components 44 to regulate a flow of electric current to light source 42. Dial 50 is at least partially accessible from the exterior 26 by the user 48 to enable control of the brightness of emitted light from light source 42 according to user 48 preference. Adjusting means 50 can also serve as a master power on/off switch for the attachment assembly 12. Additional adjusting means 50 suitable for use with the present technology may be readily envisioned by persons having ordinary skill in the art.

Figure 1C:
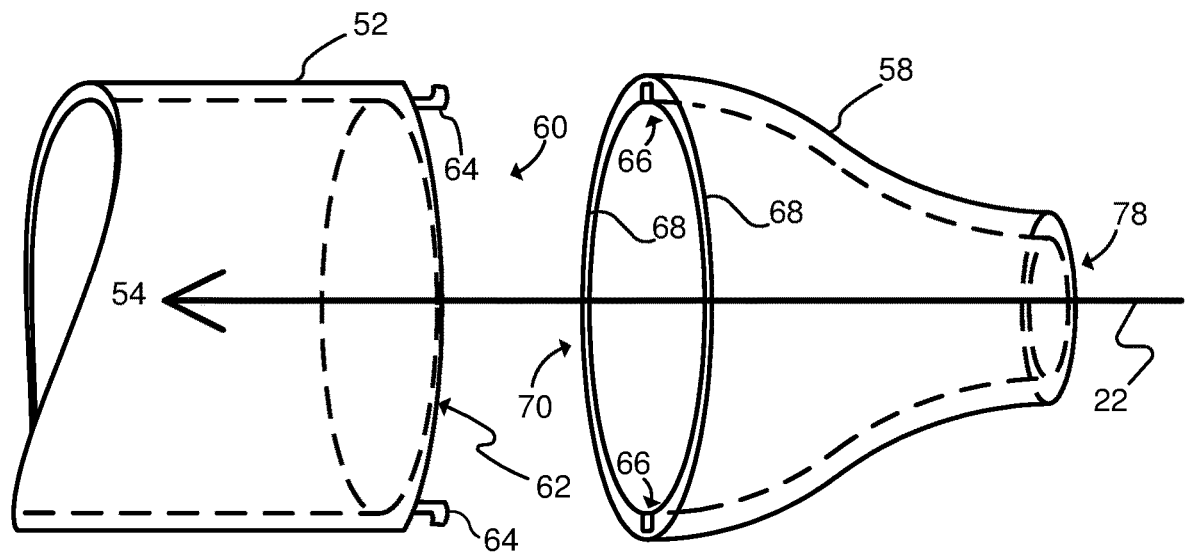

Attachment 12 can include a head 52 at least partially disposed in the cavity 38 of body 28. Head 52 can include an at least partially hollow cavity 54 inside of which a lens array 56 may be housed. In some embodiments, light source 42 is housed in cavity 54 either instead of, or in addition to, being housed in cavity 38. Head 52 can include a means 60 for attaching a speculum 58 to one side 62 of head 52 opposite body 28 side 32. As shown in FIG. 1C, the attaching means 60 can include two or more tabs 64 extending axially outward from portions of side 62 for mating with corresponding spaces 66 between tabs 68 on a broad side 70 of speculum 58. User 48 can align the tabs 64 with spaces 66 and so place the speculum 58 removably yet securely onto head 52. In other embodiments, not shown, the attaching means 60 can be screw threads into, or on, which corresponding threads proximal broad side 70 may be turned to alternately place and remove speculum 58 onto and from head 52. Additional attaching means 60 suitable for use with the present technology may be readily envisioned by persons having ordinary skill in the art.

Further disposed in one or both of body cavity 38 and head cavity 54 may be at least one means 71 for redirecting light such as a light pipe or other structurally and functionally suitable light-redirecting element 71. A means 72 for adjusting a position of light-redirecting element 71 can be operably coupled to element 71. In the illustrated embodiment, the adjusting means 72 is a lever device 72 operably coupled to light-redirecting element(s) 71 and is at least partially accessible from the exterior 26 by the user 48 to enable control of the directionality of light emitted from light source 42 and further through a first opening 73 in body 28, as desired by user 48. Additional adjusting means 72 suitable for use with the present technology may be readily envisioned by persons having ordinary skill in the art.

In some embodiments, a portion of head 52 proximal its side 62 can extend through the first opening 73 of body 28, as shown in FIG. 1A. First opening 73 provides access to cavity 38 from a body side 74 opposite side 32. First opening 73 can enable head 52 to be removably positioned inside of, and optionally on, portion(s) of body 28 to facilitate use of various design configurations of optics (e.g., lens array 56) or light sources 42 for different examination subjects or operational scenarios. For example, a first head 53 can have a lens array 52 providing a greater level of illumination, or optical magnification, of object(s) 24 as compared to a second head 52.

Body 28 can include a second opening 76 on its side 32 to provide a continuous axial path for light 22 to be transmitted from object(s) 24 to imaging device 16 through a proximal opening 78 of speculum 58 and further through head 52 and lens array 56. The attaching means 60 prevents stray light from entering this desired light path 22.

FIGS. 2A-2O, 3A-3G and 4A-4E depict a set of two-dimensional, sectional and perspective views of a smartphone otoscope attachment assembly 101, according to an embodiment of the present technology. Assembly 101 can include any of the features of mobile imaging device attachment 12, as shown and described above with reference to FIGS. 1A-1C, and as such FIGS. 2A-2O, 3A-3G and 4A-4E share some of the same feature numbers as FIGS. 1A-1C. Assembly 101 can include a cover 103 removable attached to at least a portion of body 28. Cover 103 enables user 48 to alternately open and close cavity 38 as needed to gain access to cavity 38 for purposes such as inspection, maintenance, and changing or testing power supply 40 batteries. FIGS. 2A-2O and 4A-4E depict assembly 101 with the cover 103 on, and FIGS. 3A-3G depict assembly 101 with the cover 103 off.

Figure 2A:
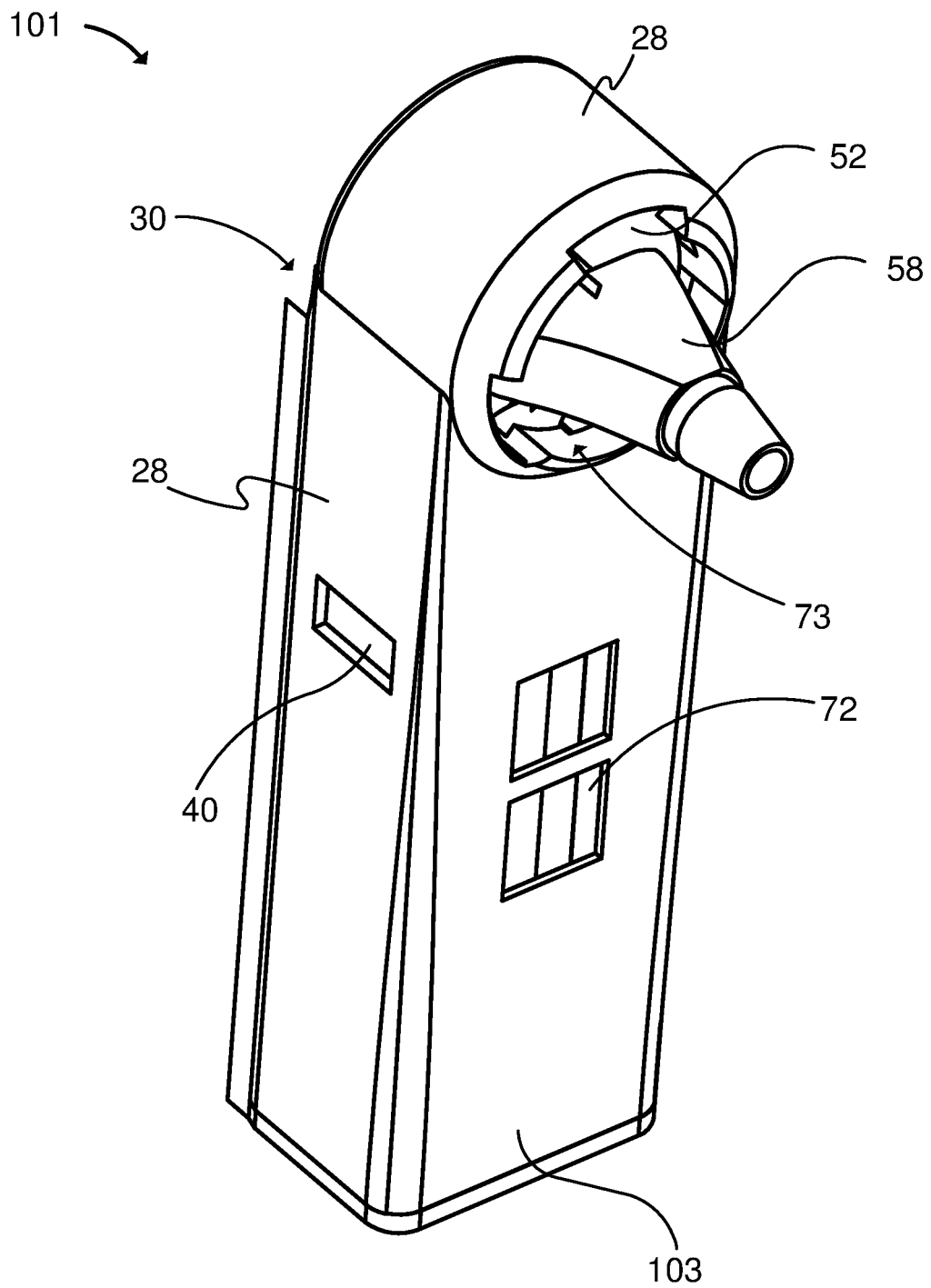
FIGS. 2A-2O depict a set of two-dimensional, perspective and sectional views of a smartphone otoscope attachment assembly, according to an embodiment of the present technology.
Figure 2B:
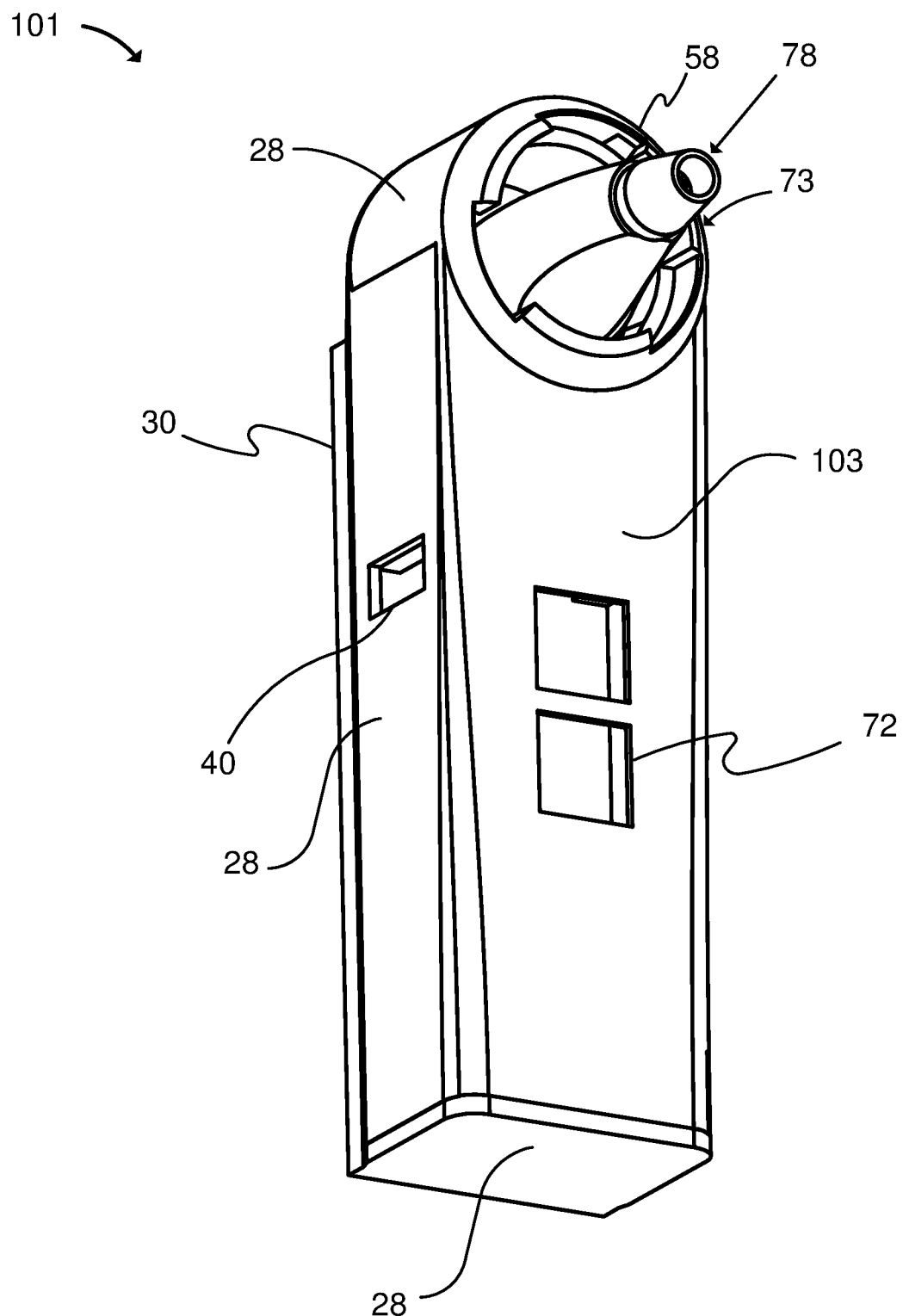
Figure 2C:
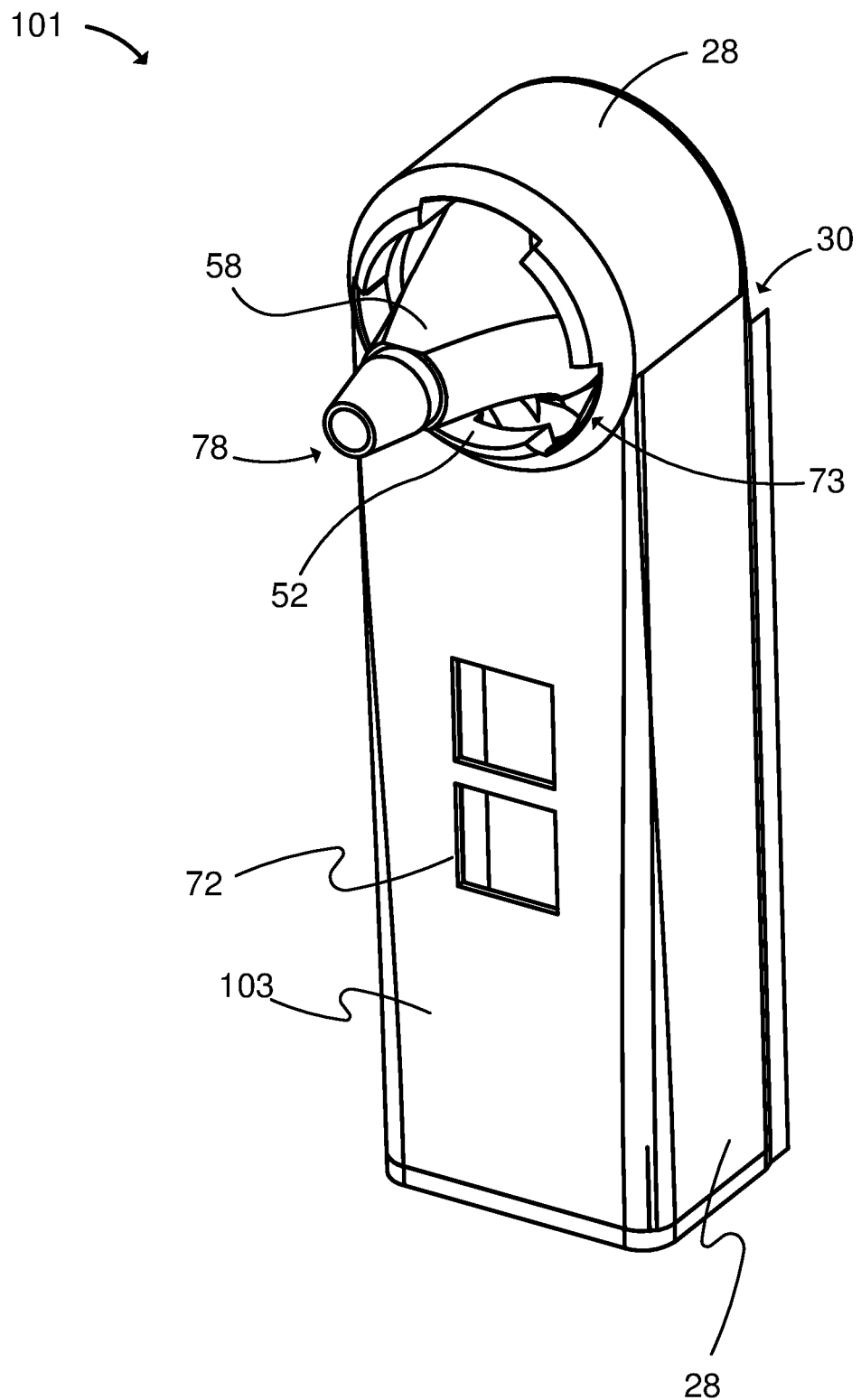
Figure 2D:
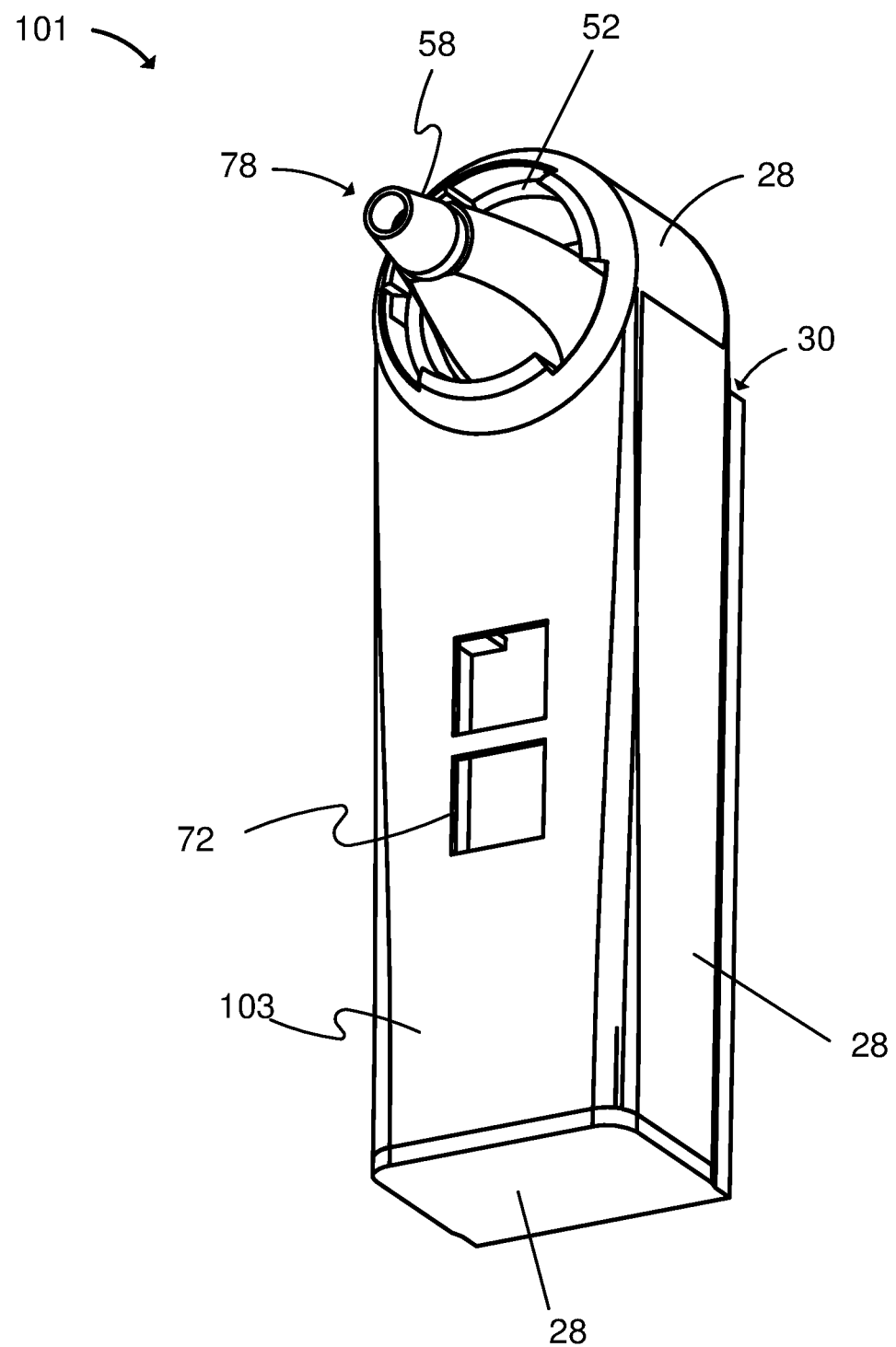
Figure 2E:
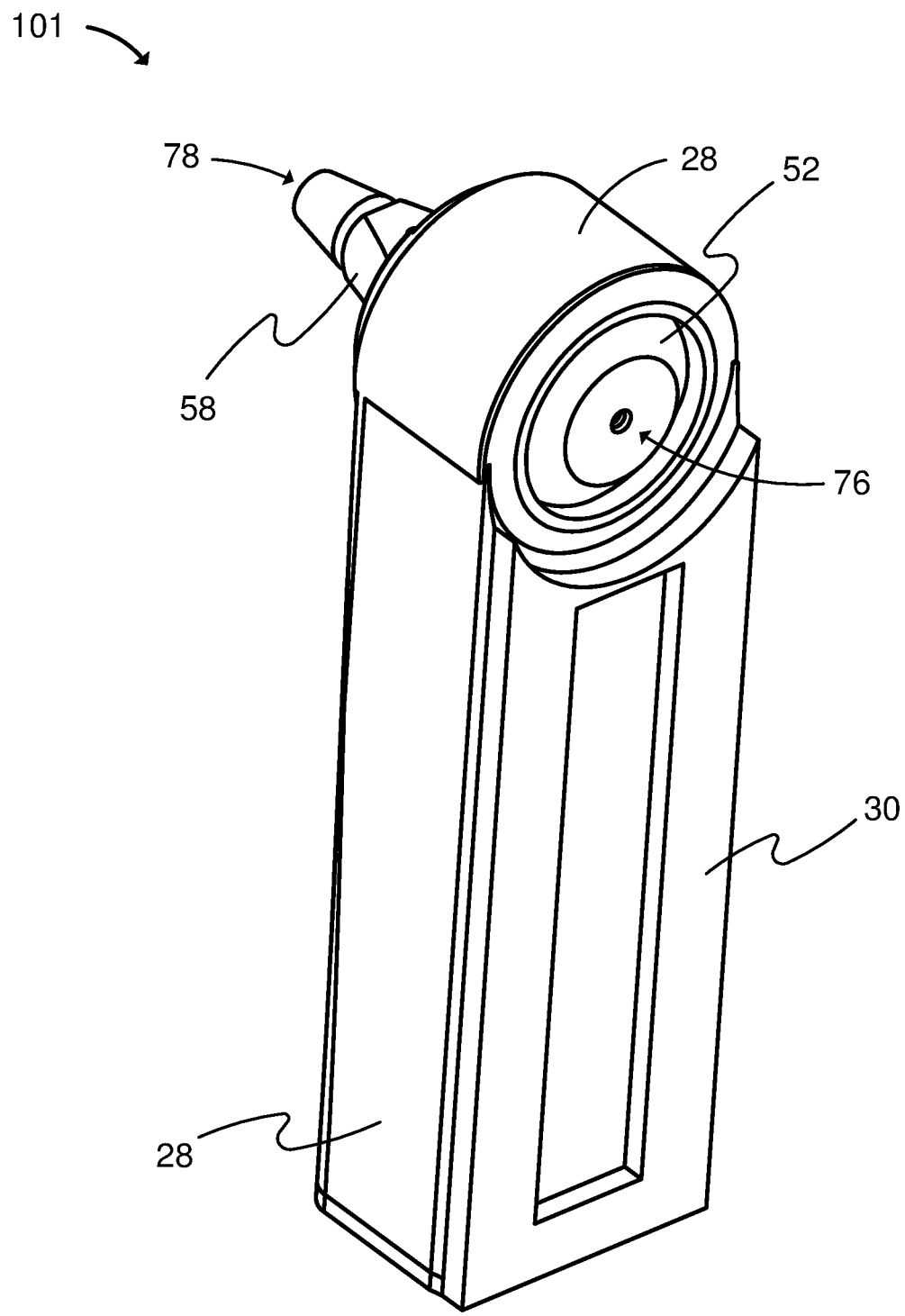
Figure 2F:
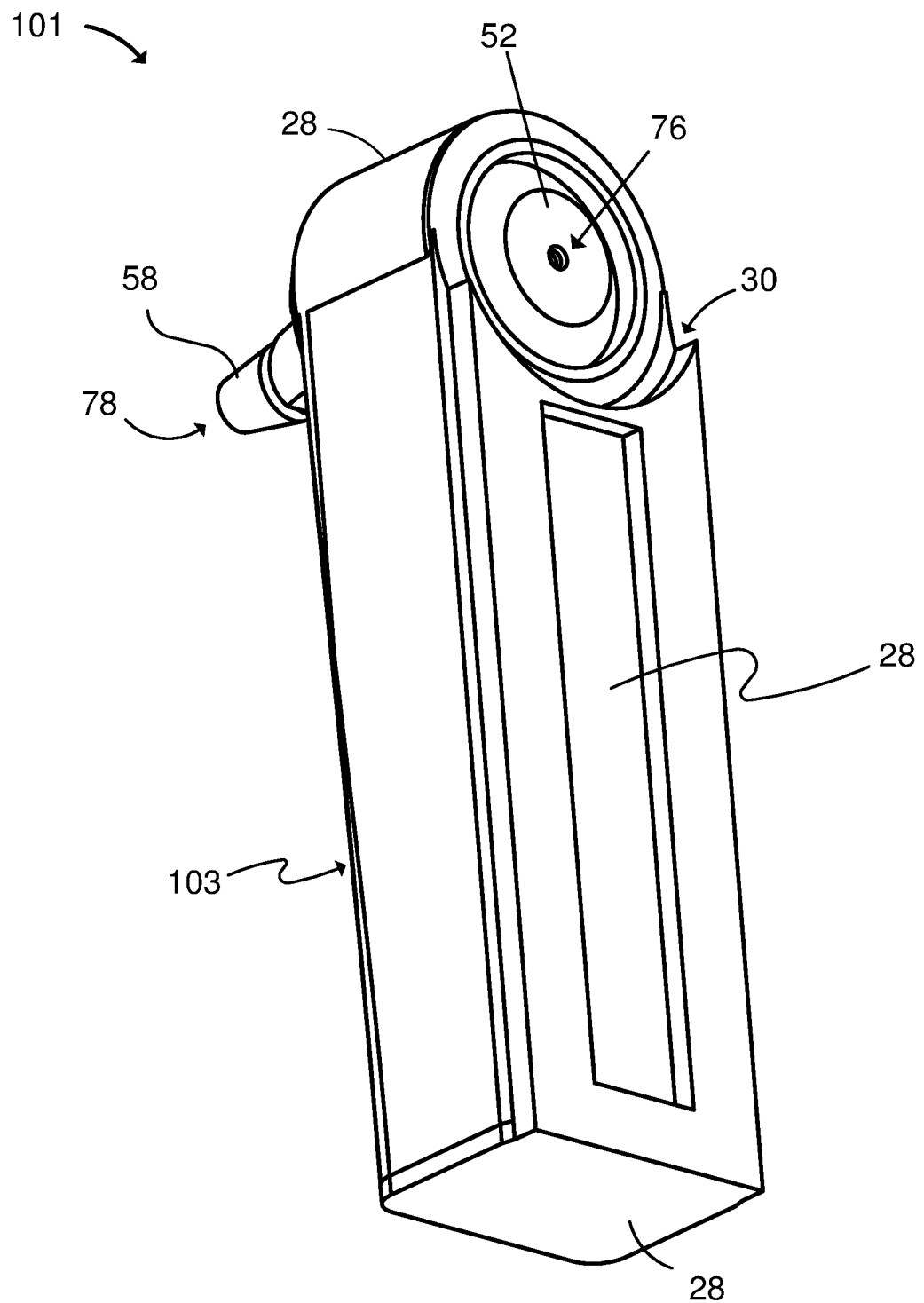
Figure 2G:
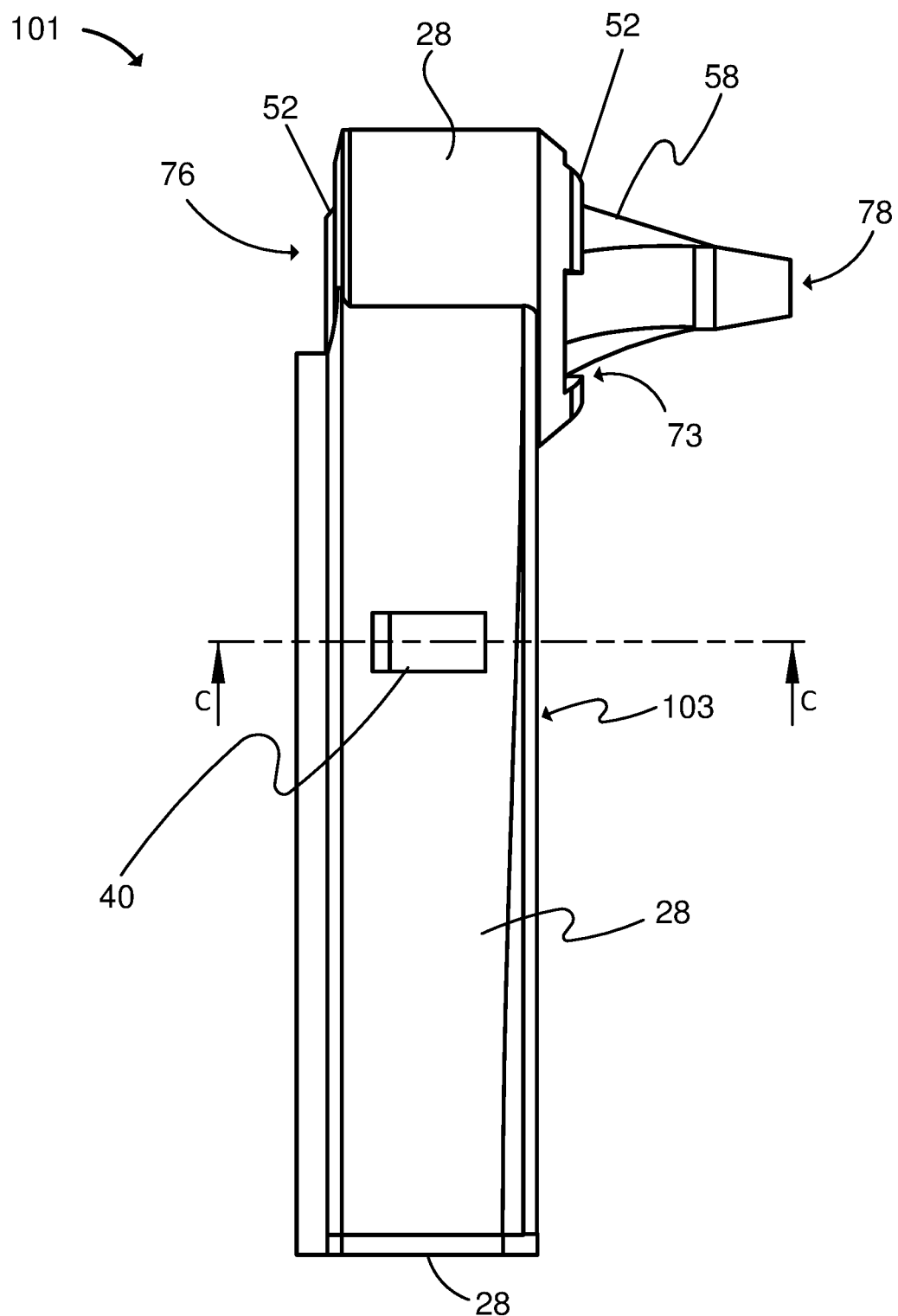
Figure 2H:
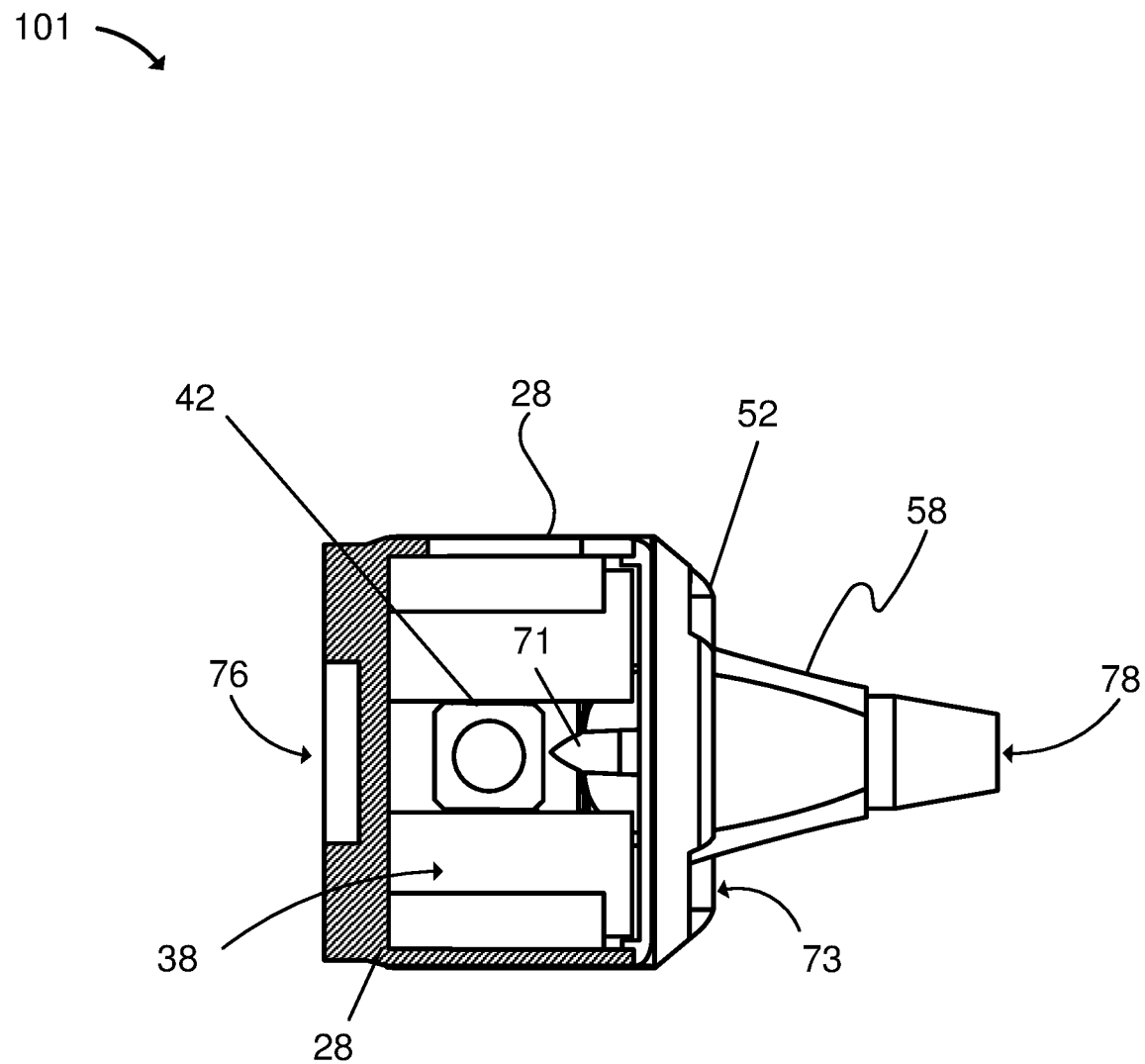
Figure 2I:
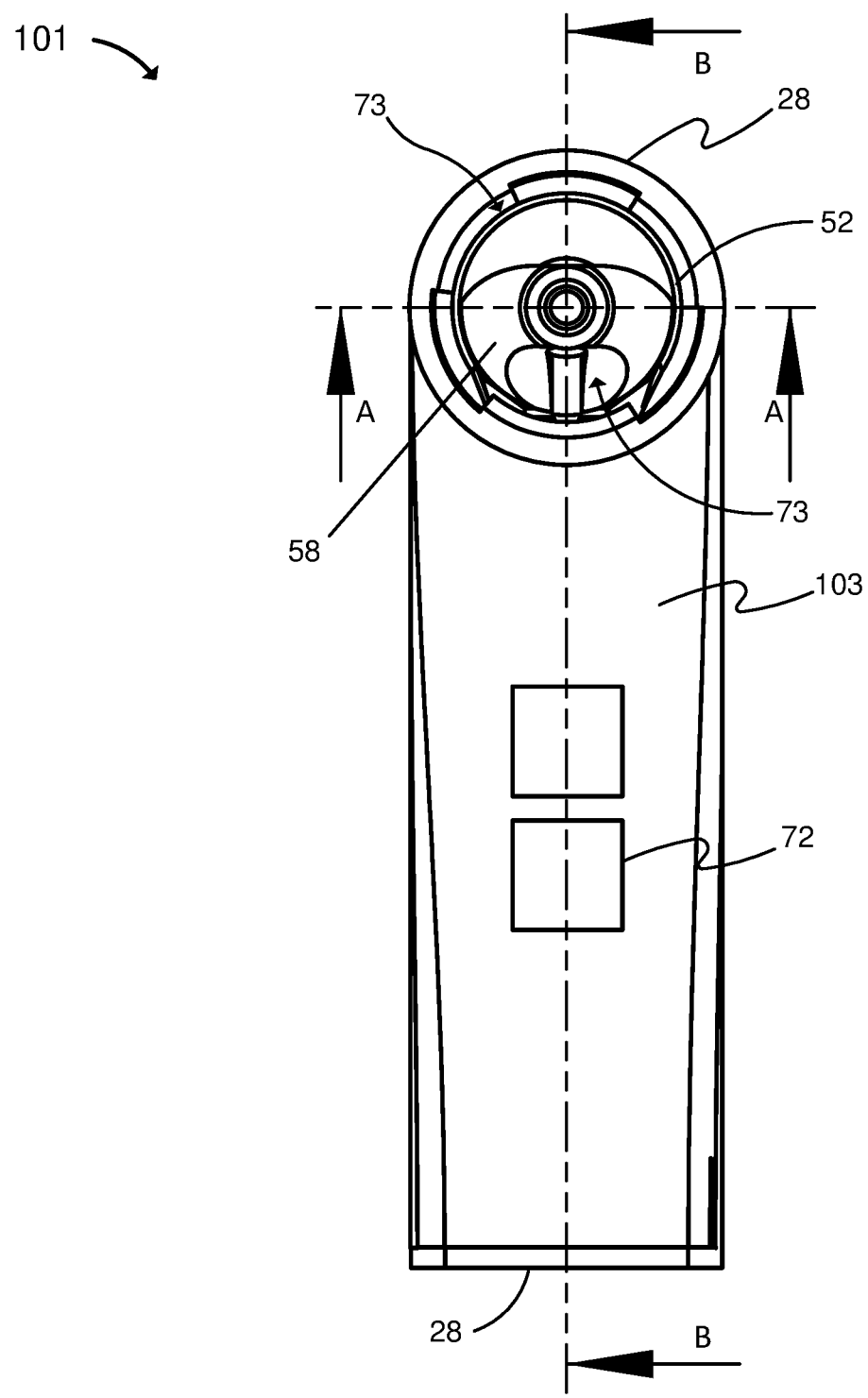
Figure 2J:
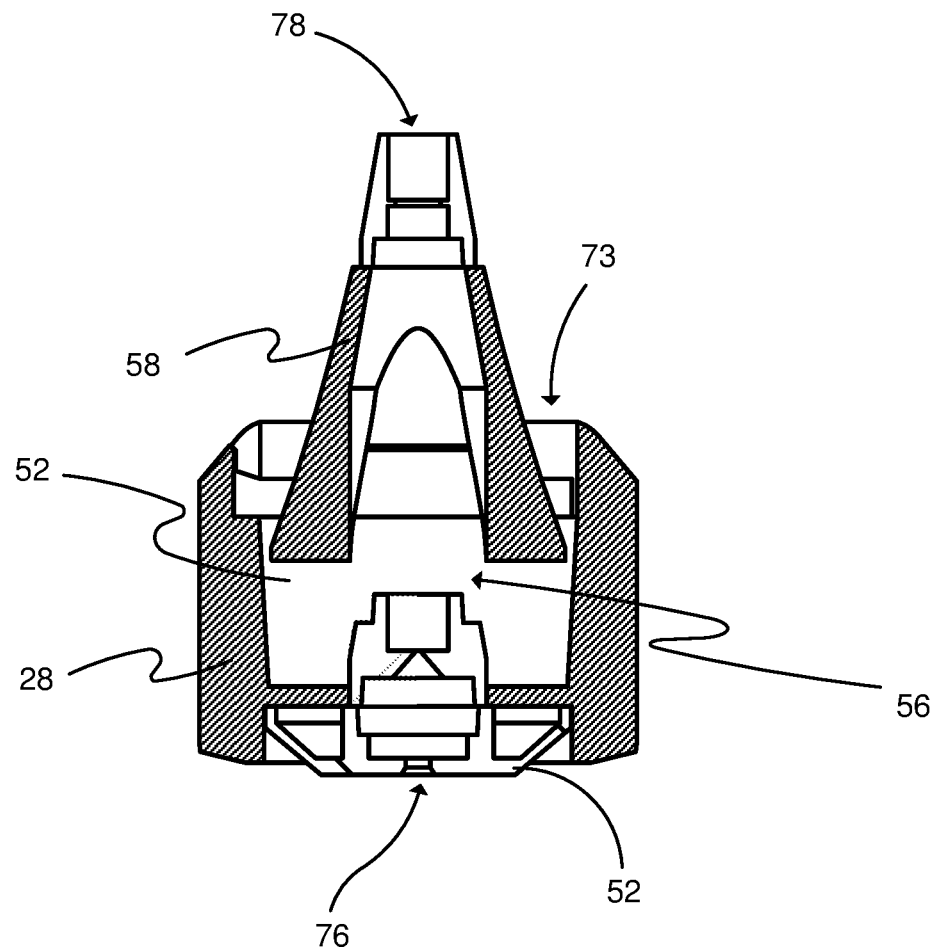
Figure 2K:
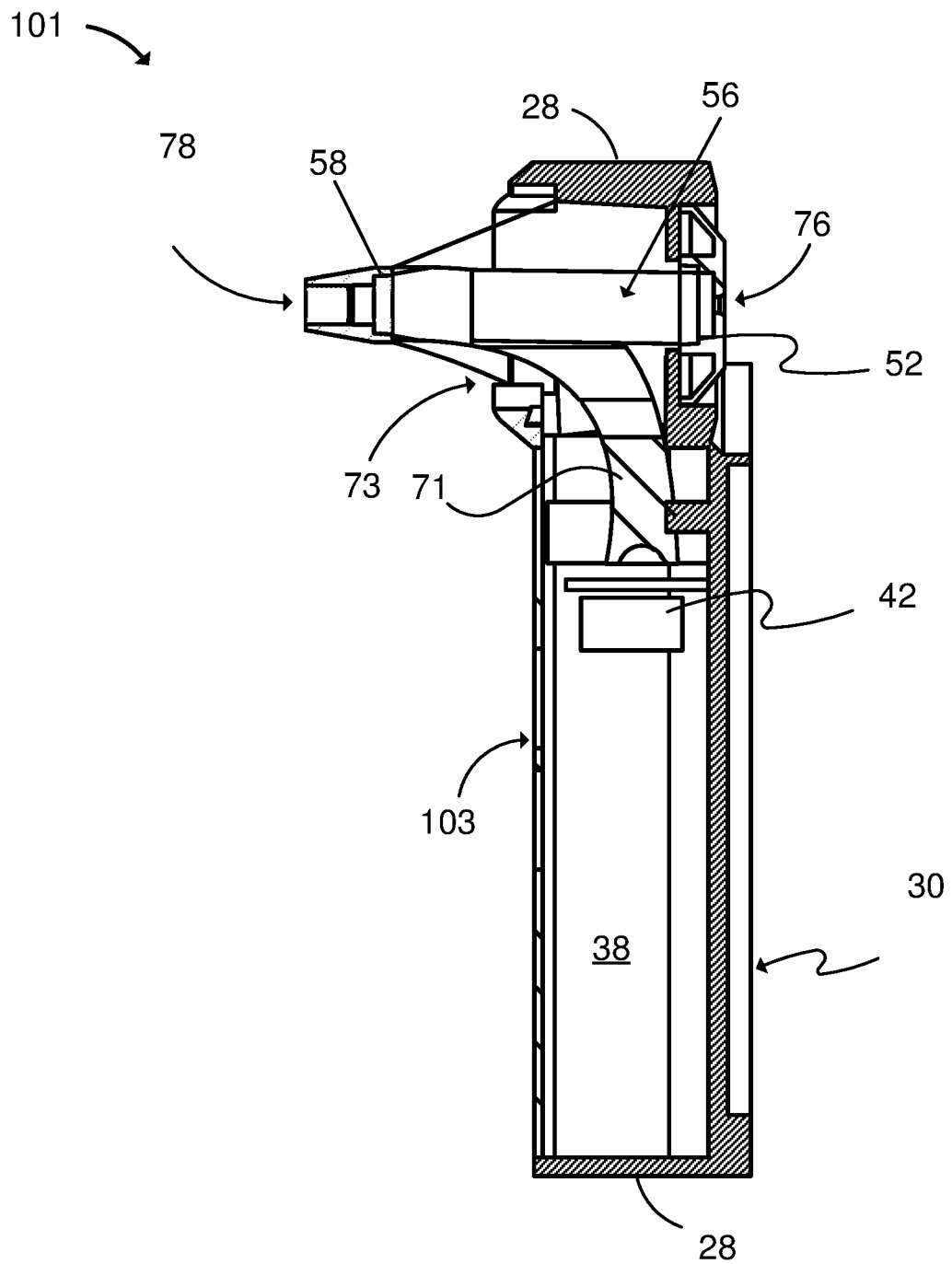
Figure 2L:
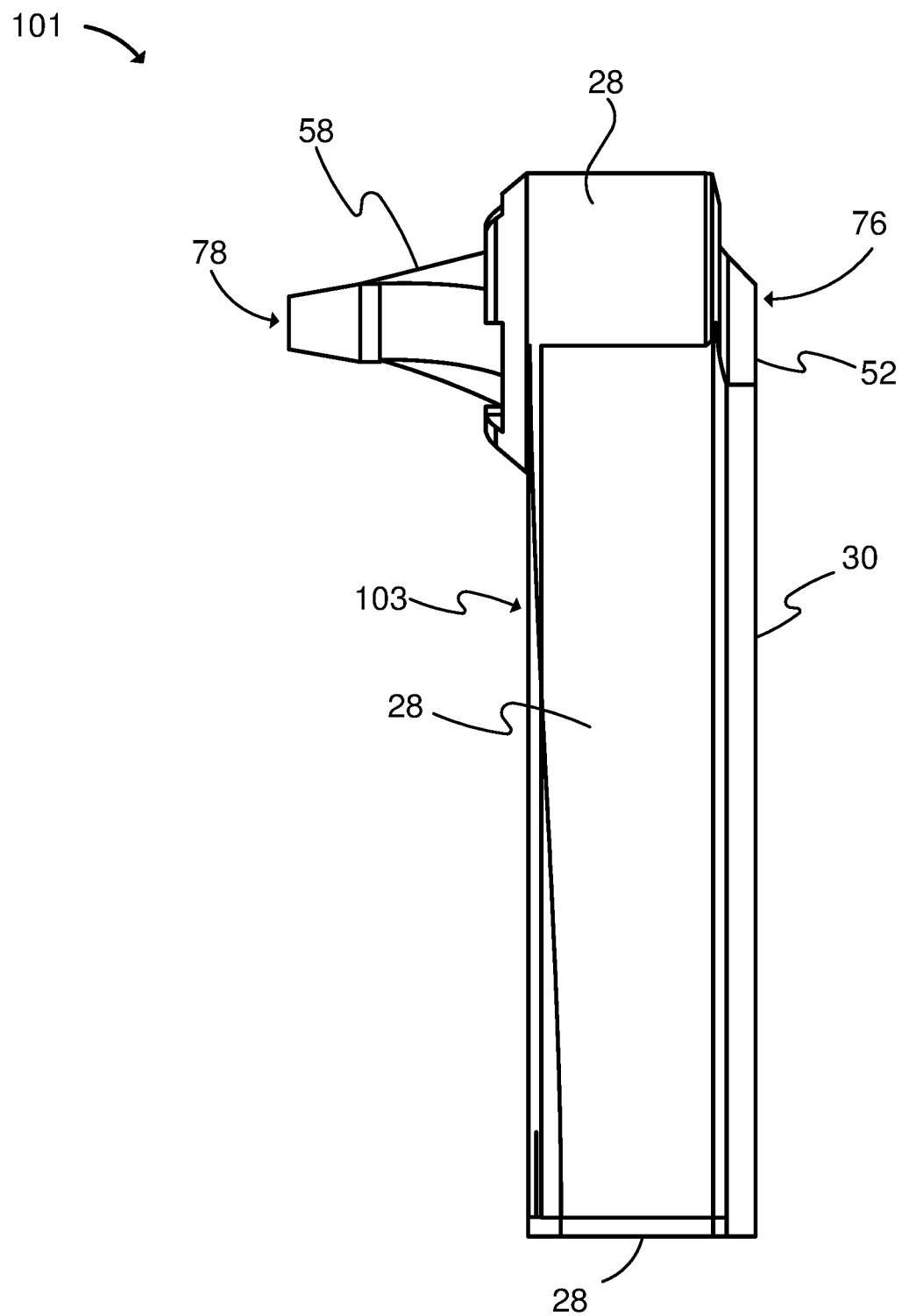
Figure 2M:
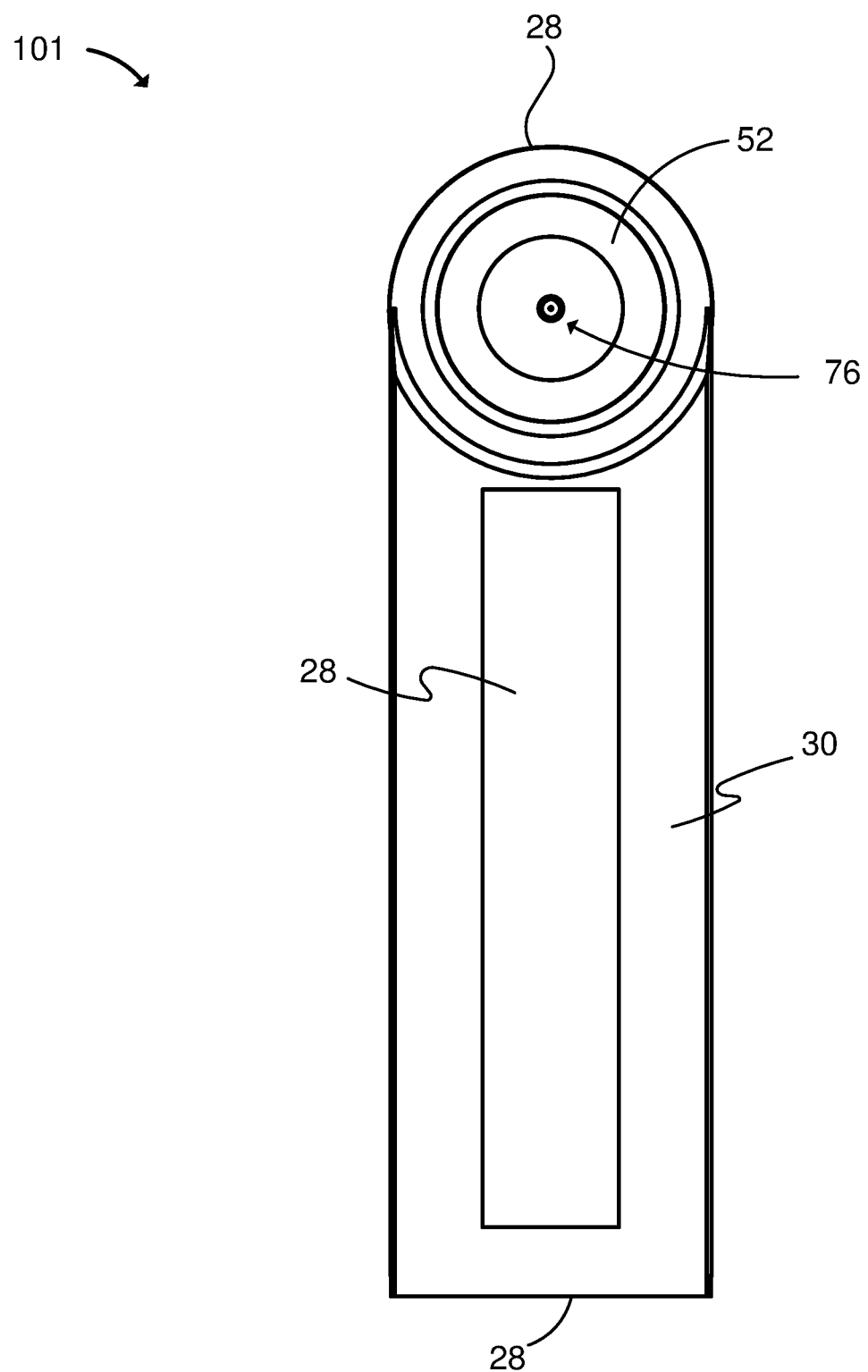
Figure 2N:
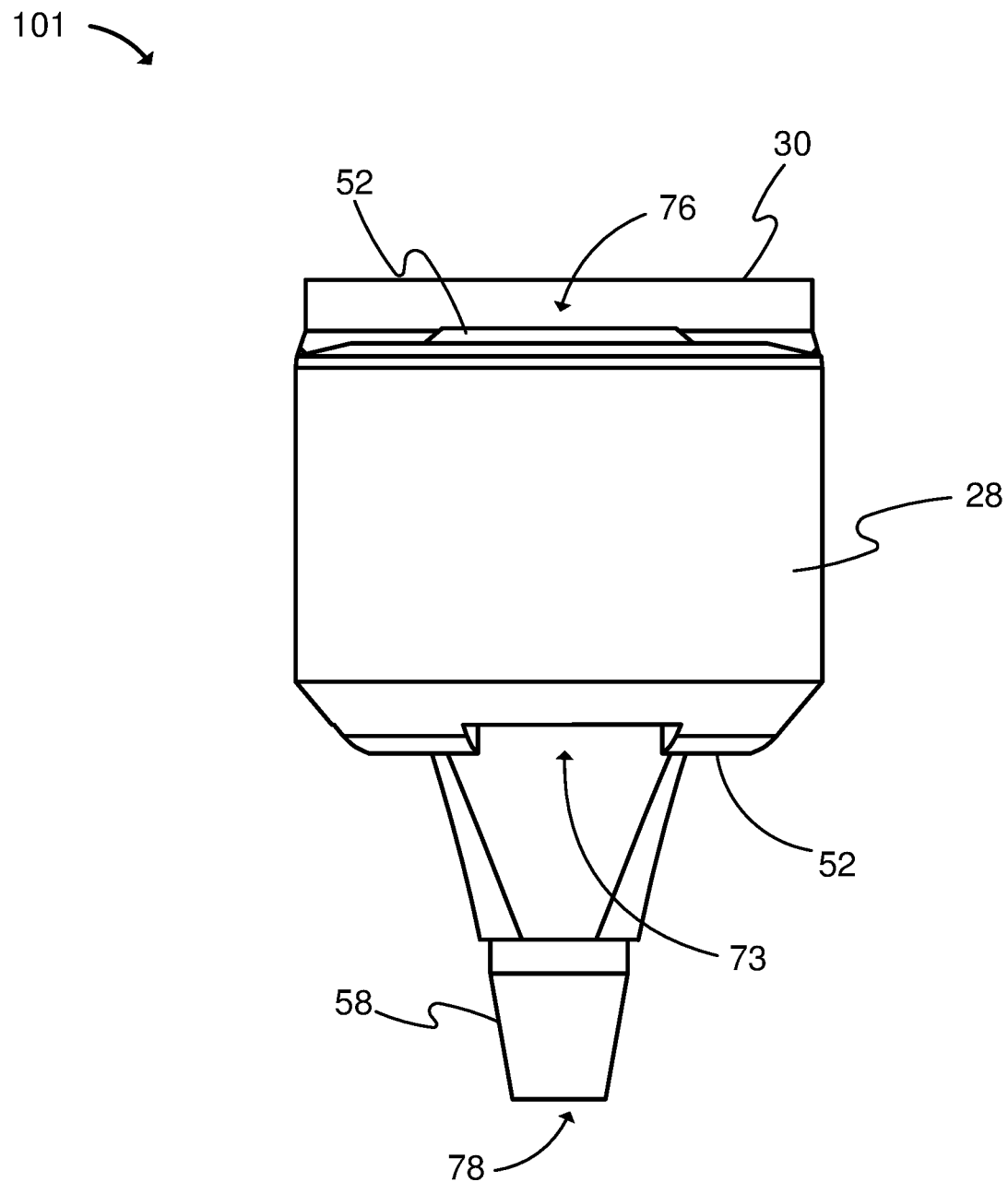
Figure 2O:
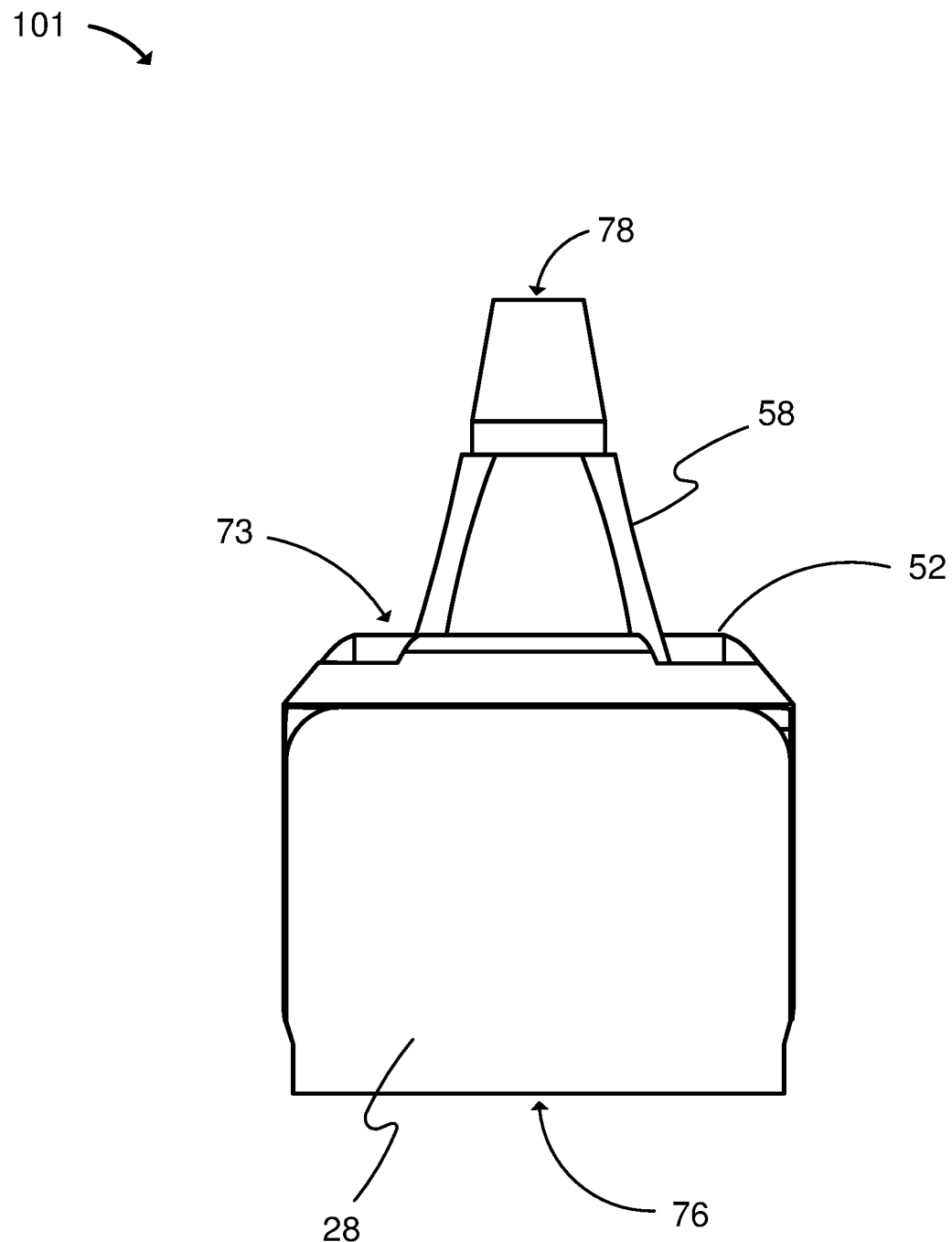
Figure 3A:
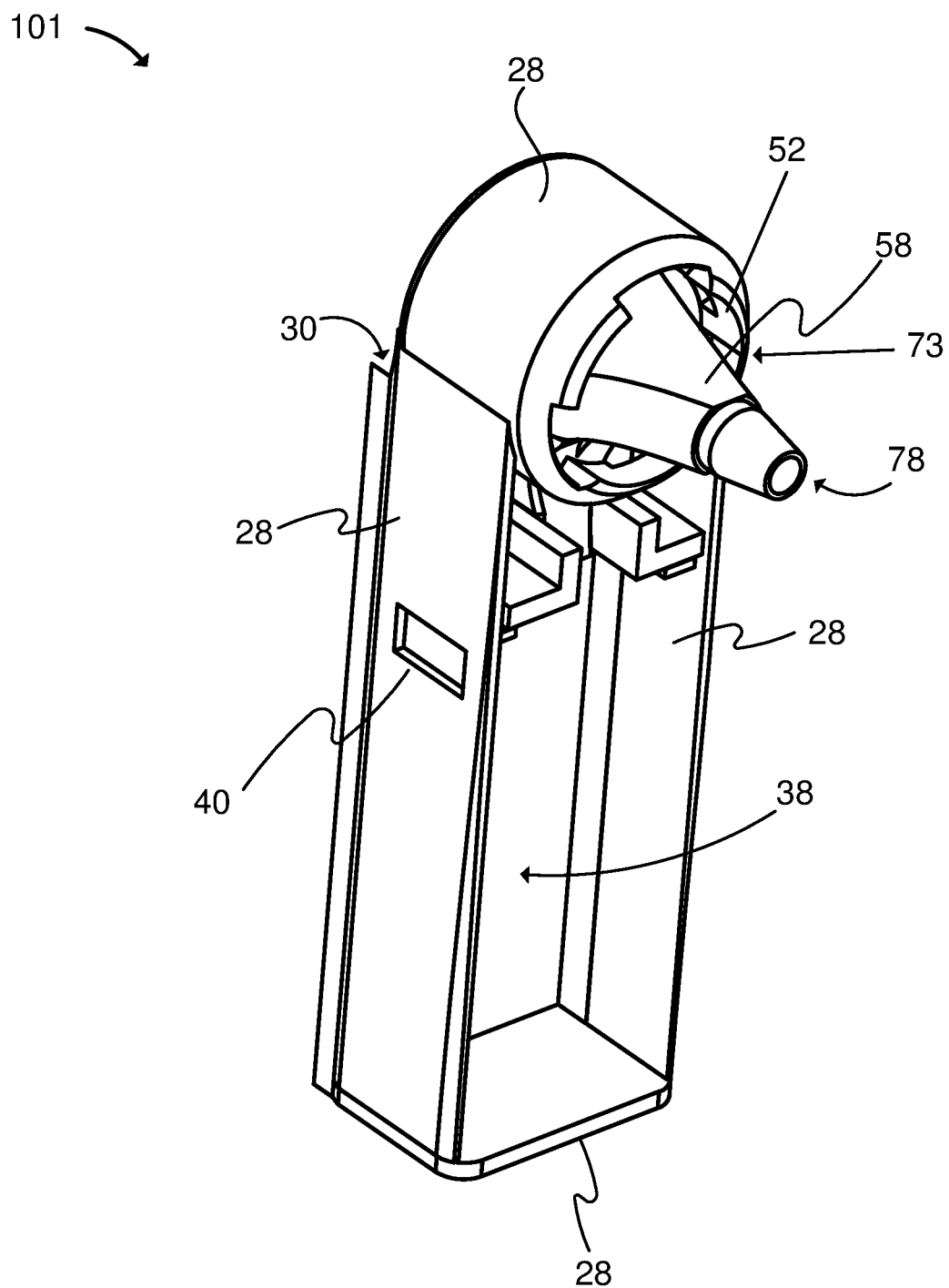
FIGS. 3A-3G depict a set of two-dimensional, perspective and sectional views of the assembly of FIGS. 2A-2O with its cover removed.
Figure 3B:
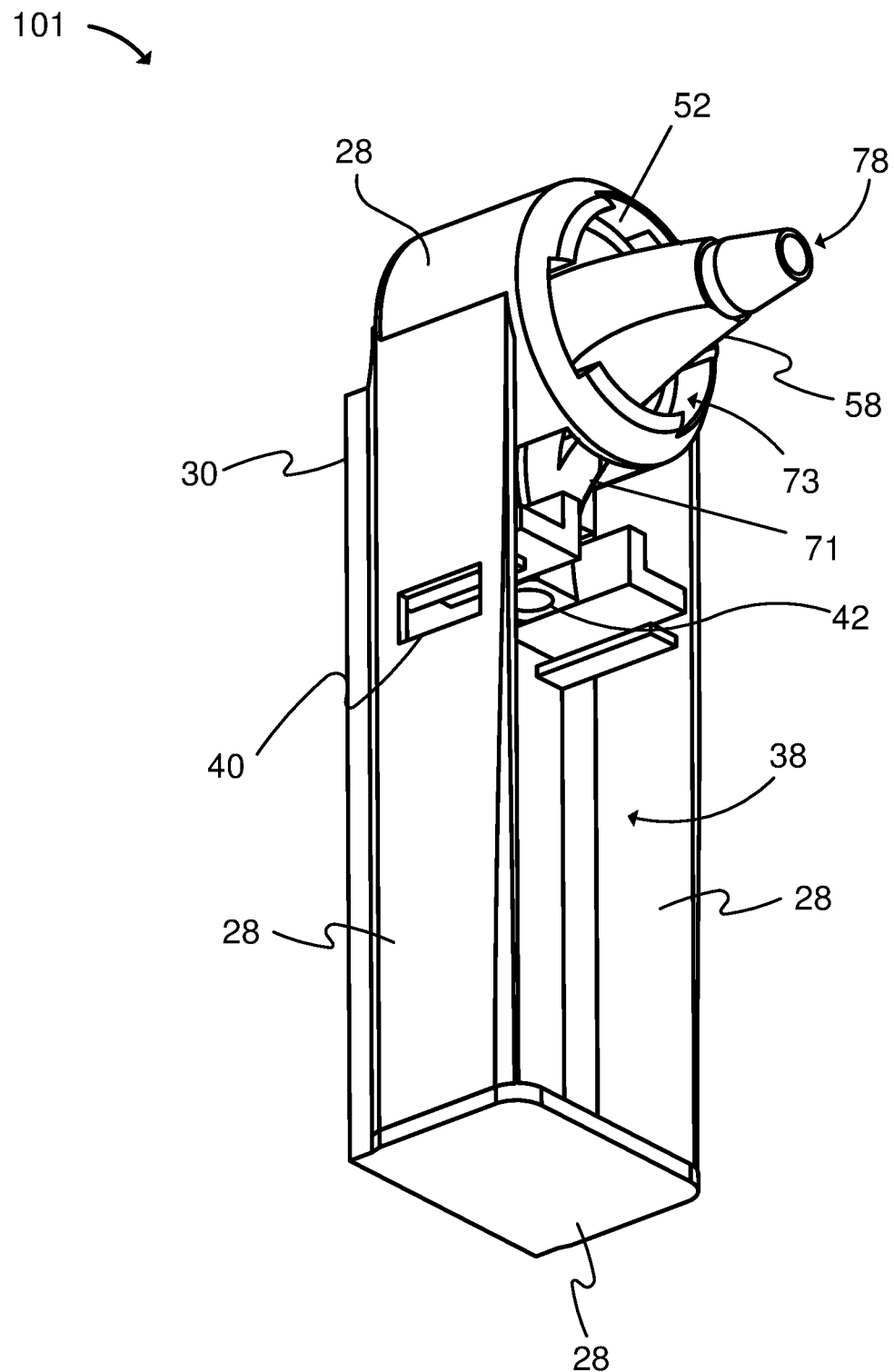
Figure 3C:
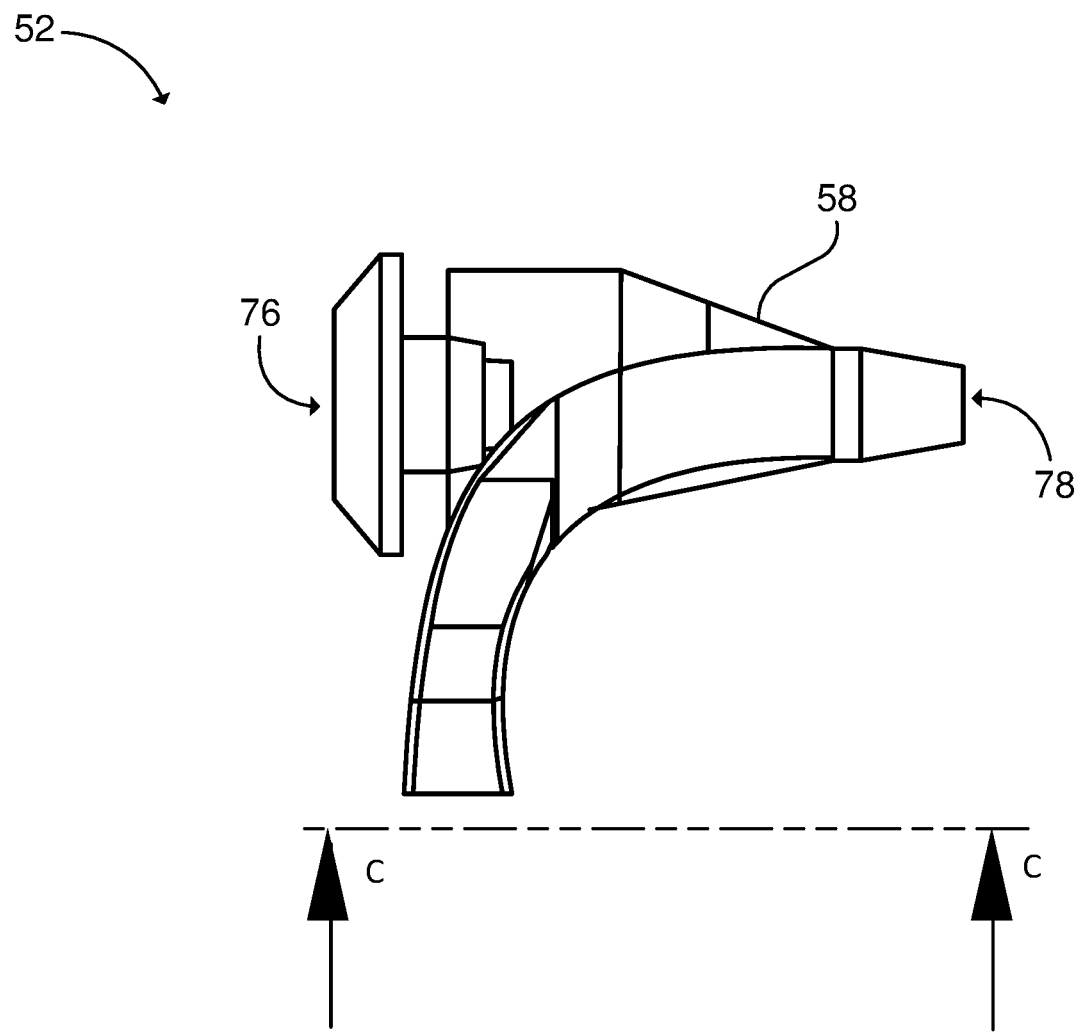
Figure 3D:
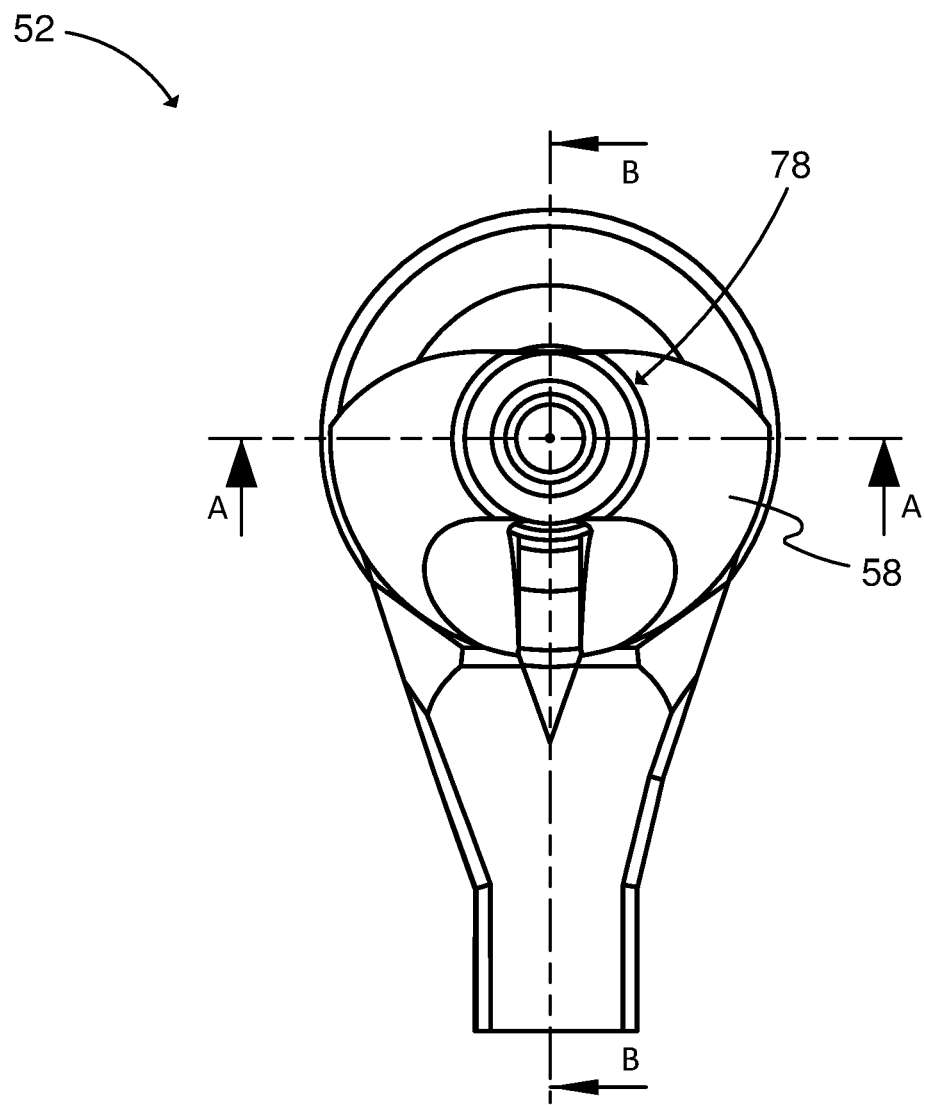
Figure 3E:
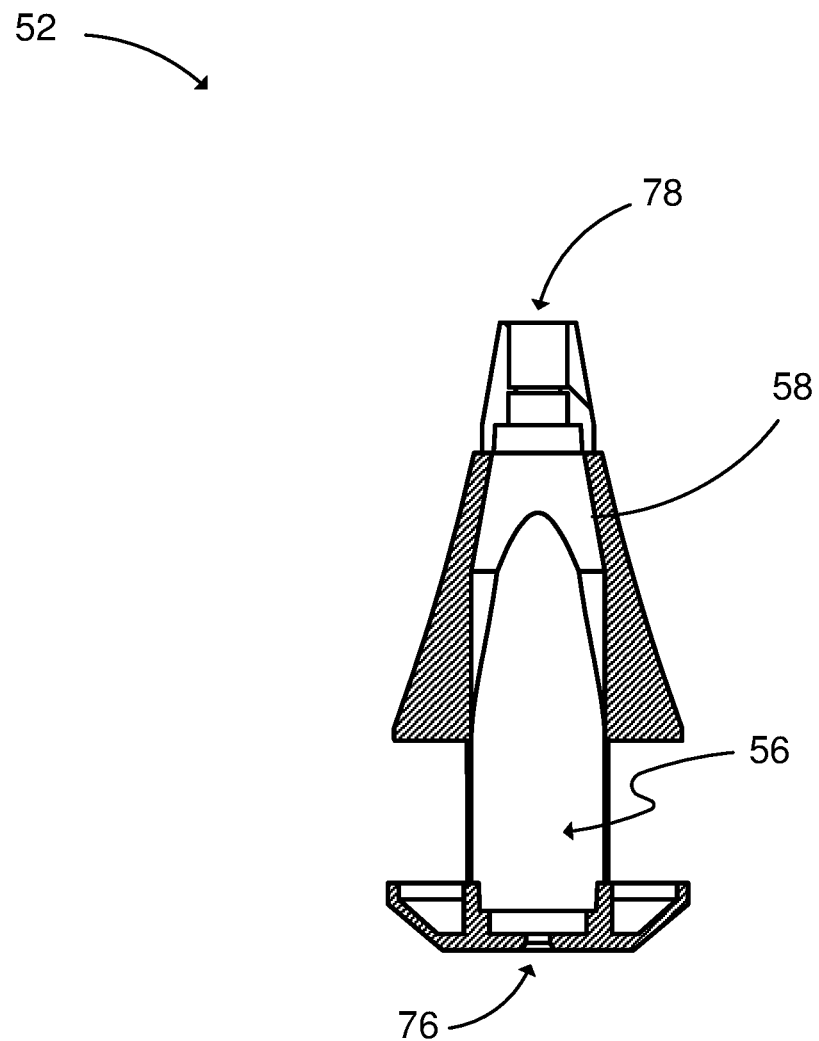
Figure 3F:
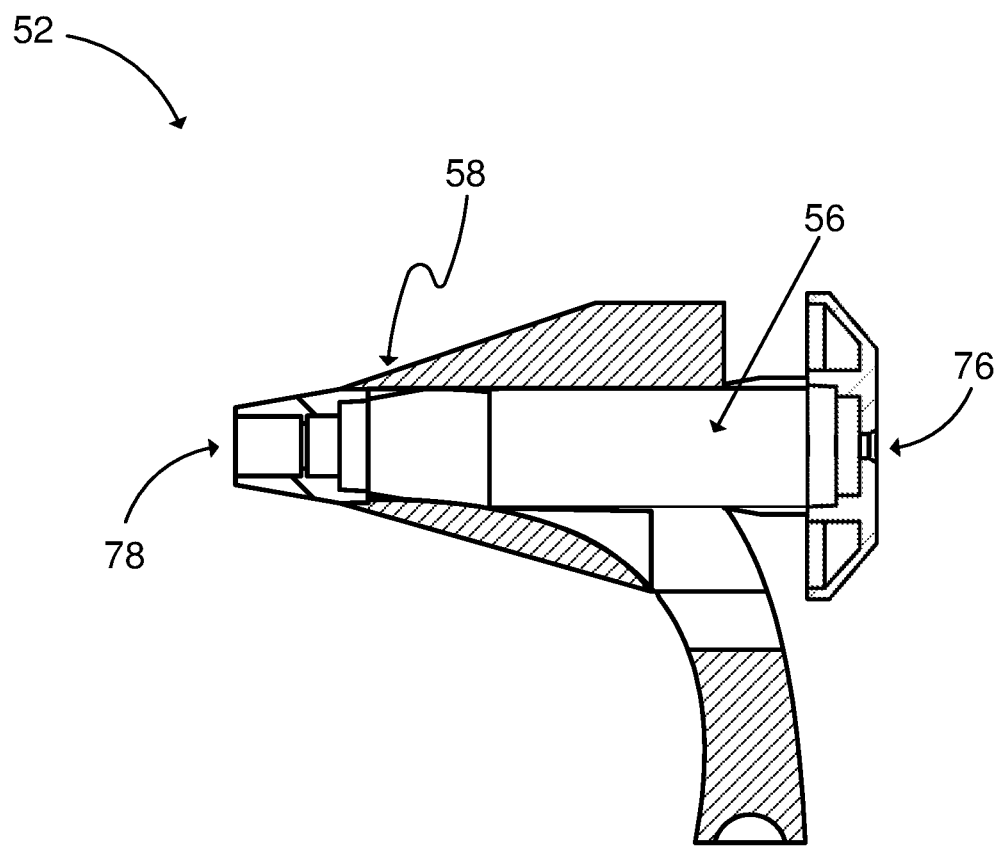
Figure 3G:
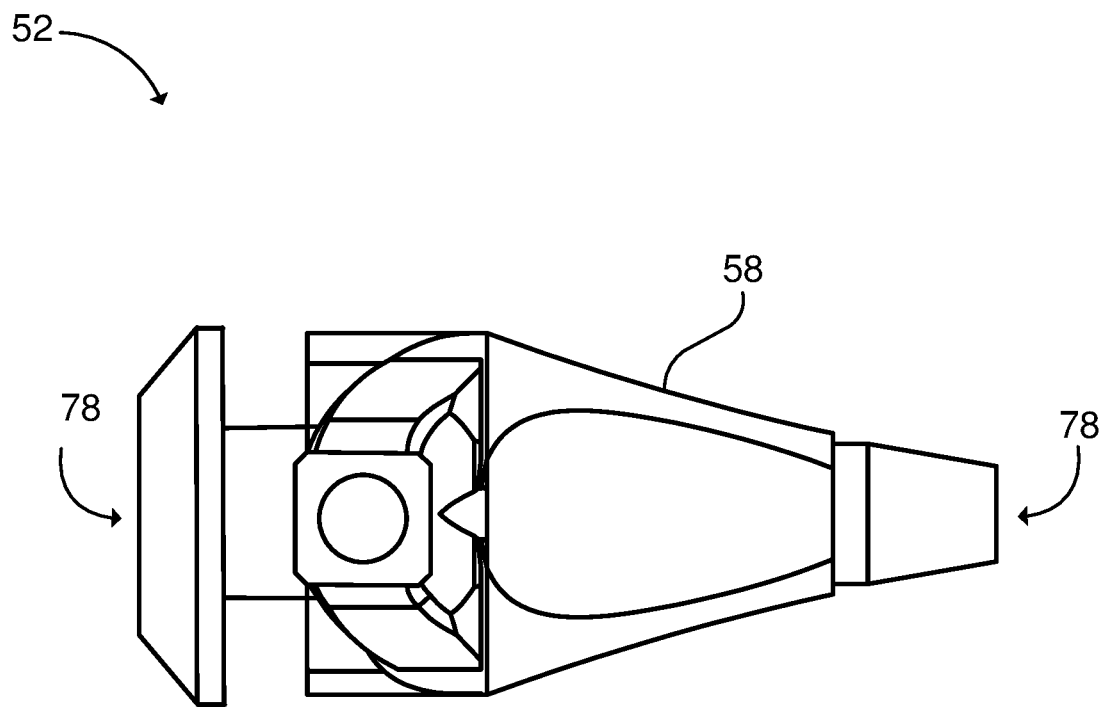
Figure 4A:
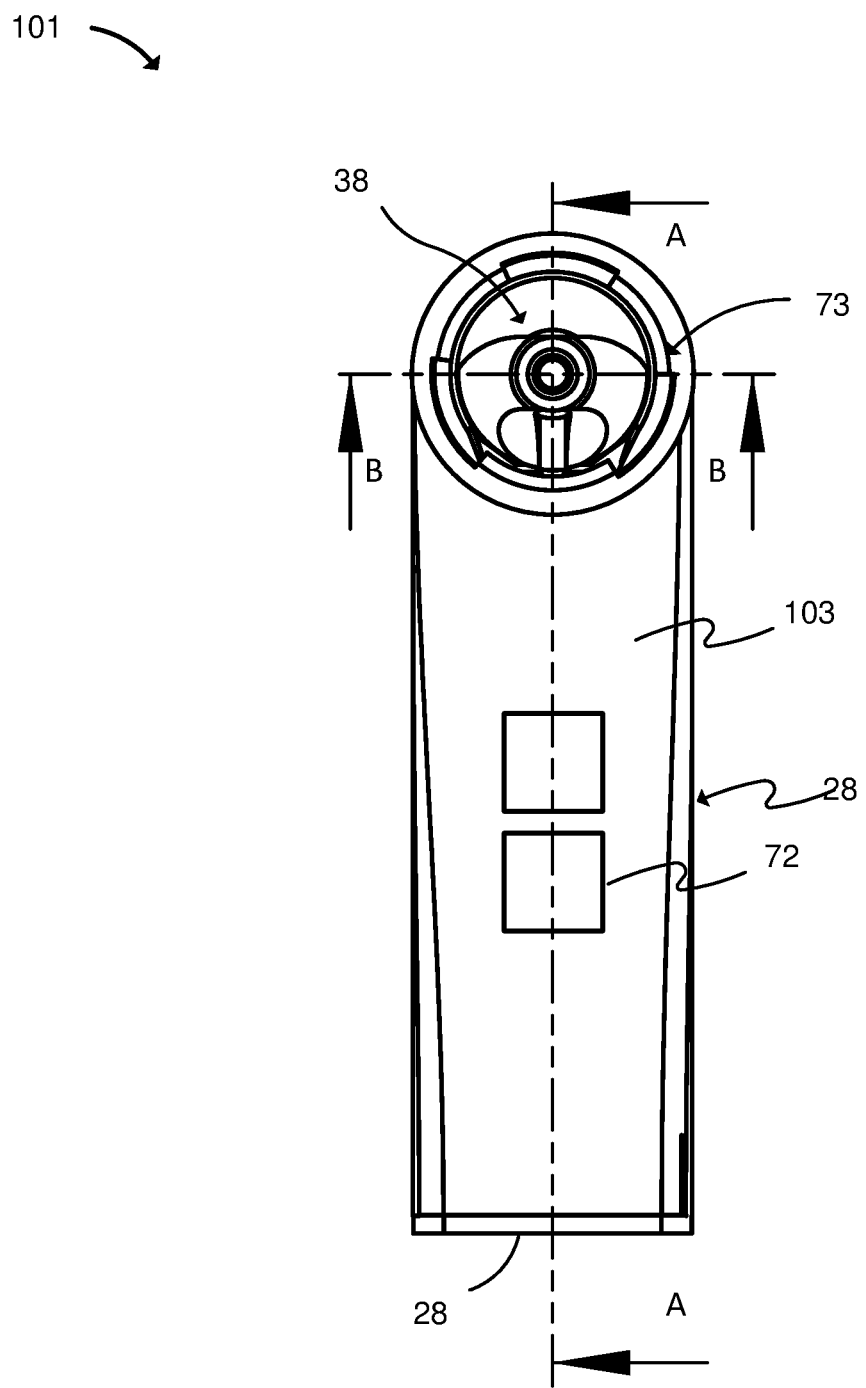
FIGS. 4A-4E depict a set of two-dimensional and sectional views of the assembly of FIGS. 2A-2O and 3A-3G with its head removed.
Figure 4B:
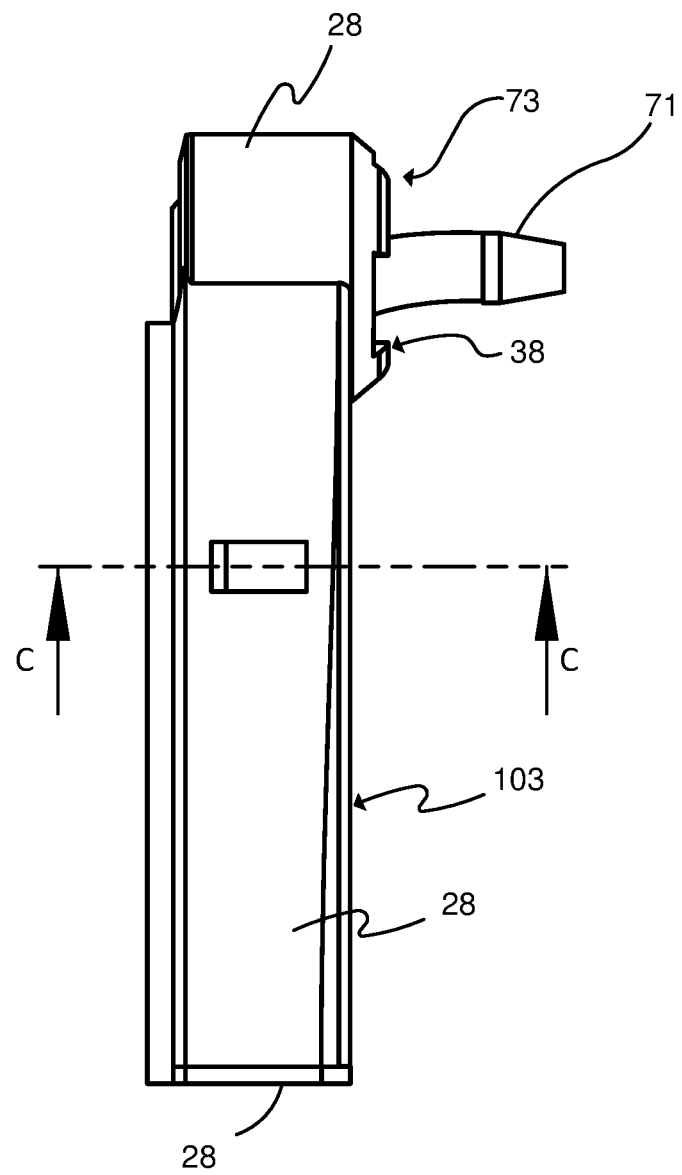
Figure 4C:
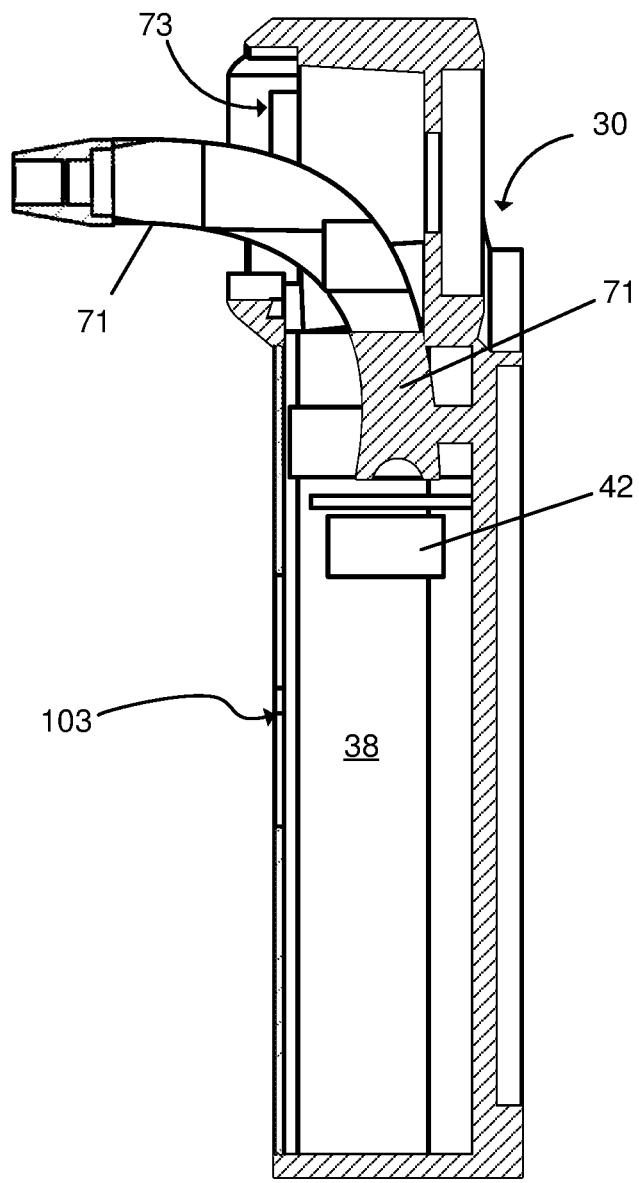
Figure 4D:
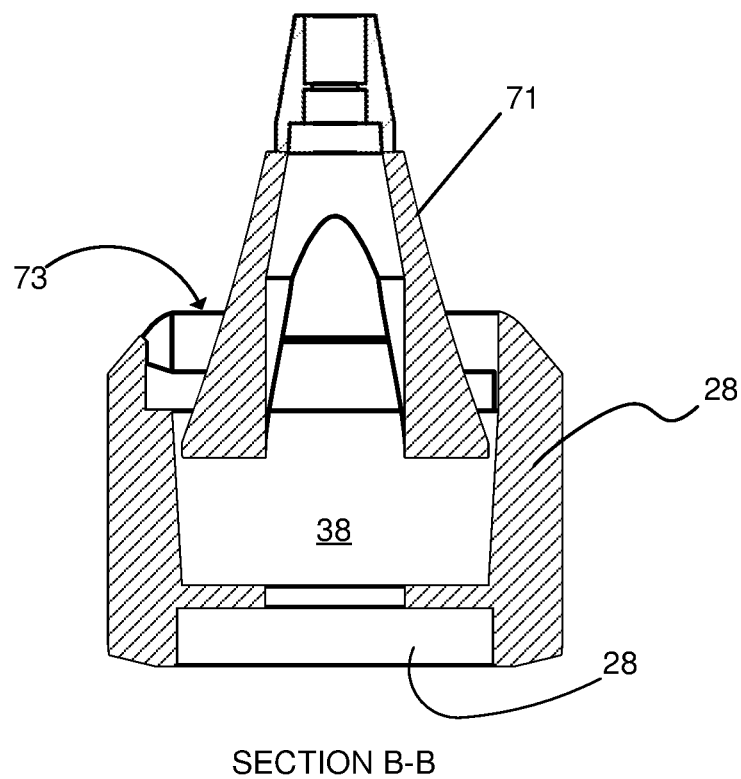
Figure 4E:
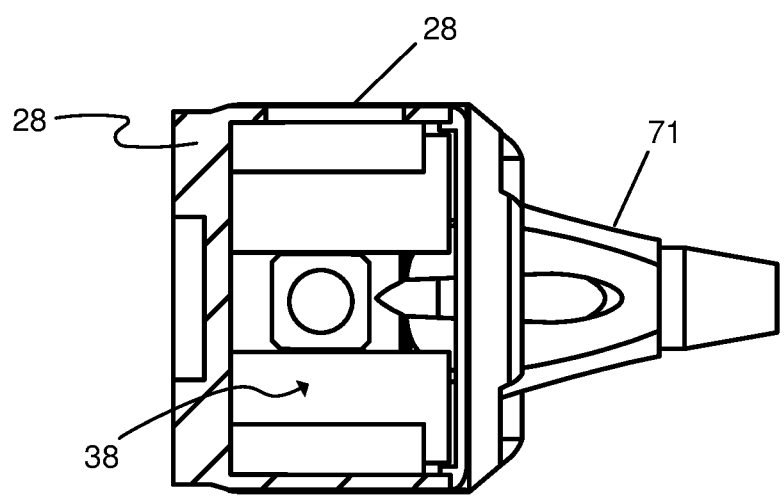

In some embodiments, the head 52 of assembly 101 is removably attached to a portion of body 28 through first opening 73. Head 52 can be inserted into, and removed from, body 28 through first opening 73 either with speculum 52 attached to head 52, or with speculum 52 disengaged from head 52. In the example shown in FIGS. 4A-4E, light-redirecting element 71 is disposed inside a portion of body 28 cavity 38 and a portion of element 71 protrudes out of first opening 73. The head 52 in its removed position is depicted alongside the remainder of assembly 101 in FIGS. 3A-3G. In the inserted position, head 52 fits over element 71 and into cavity 38 through first opening 38, as shown in FIGS. 2A-2O. In some embodiments, head 52 is shaped and dimensioned to facilitate user 48 fitting it into the first opening 73 to be seated snugly into portions of body 28, as shown in FIGS. 2A-2O. Likewise, interior surfaces of body 28 can include ridges, clips, and similar structures to facilitate contact with portions of head 52 to provide for the removable attachment, as described above.

Referring to FIGS. 1A-1C, 2A-2O, 3A-3G and 4A-4E, in operation, user 48 can place attachment assembly 12 (and similarly smartphone otoscope attachment assembly 101) with speculum 52 onto the back 20 of smartphone 10 by way of attaching means 30. Alignment of the aforementioned light path 22 can be assessed by the user 48 by activating the smartphone camera and ascertaining whether the field of view is obscured in any way. If the field of view is obscured, the user 48 can adjust the position on attachment 12 on smartphone 10 in at least one of the vertical and horizontal directions, as further shown and described below with reference to Example 2. In the case of attachment assembly 12 used as an otoscope attachment, the user 48 can insert the speculum 52 into the ear of a subject, turn on and adjust the light source 42, and view the resulting image on the smartphone 10 display 14. The light source 42 can be further adjusted along with image focus and other parameters to optimize the image quality prior to storing or transmitting the image or video.

Digital images captured with the imaging device 16 by way of the attachment assembly 12 of the present technology may be incorporated into electronic medical records, facilitating documentation and review over time, an important aspect in the management of pediatric otitis media, for example. Many applications employed by hospitals and clinics on physicians' smartphones do not allow images to be uploaded or captured through a smartphones camera photo storage, as it is a violation of HIPAA policies. Using a video-otoscope according to the present technology which does not require the need to go through a third party and can be used directly through HIPAA-compliant programs and applications allows direct image input into the patient's record.

The following examples are provided to further illustrate the above described, and additional, embodiments of the present technology.

EXAMPLE 1

Figure 5:
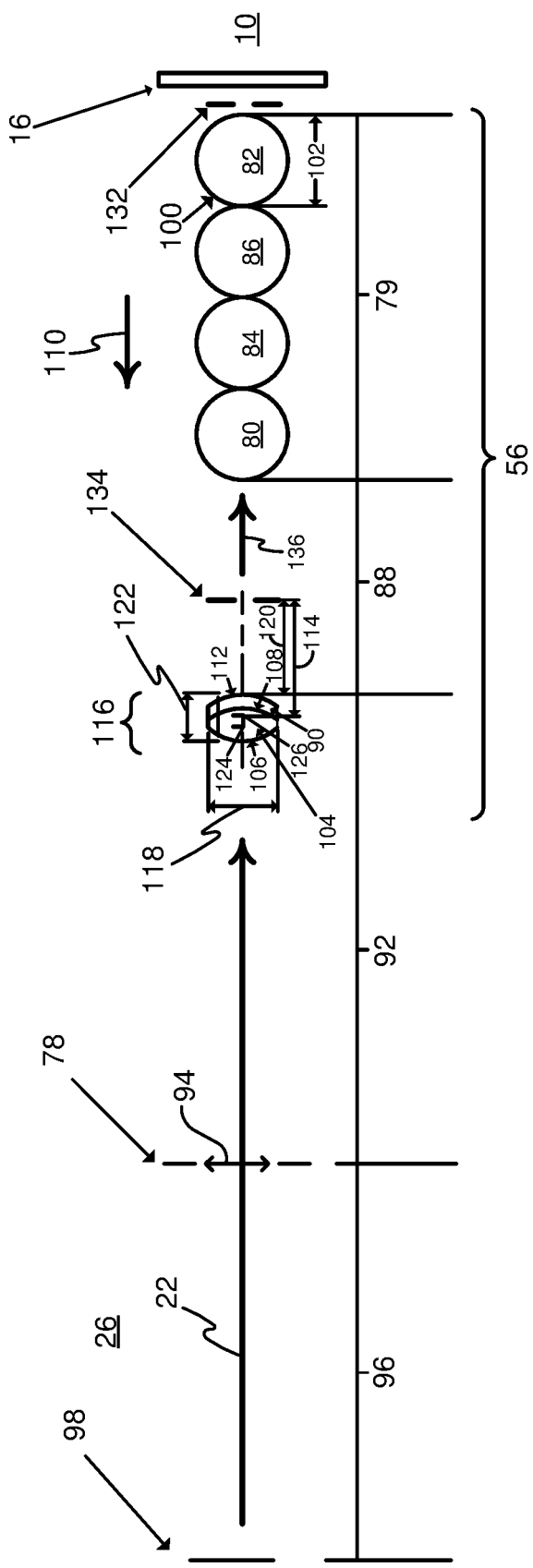
FIG. 5 depicts a schematic diagram of a lens array that may be used with the smartphone otoscope attachment assembly of 2A-2O, according to an embodiment of the present technology.

FIG. 5 depicts a schematic diagram of a lens array 56 that may be used with the smartphone otoscope attachment assembly 12 of FIGS. 2A-2O, according to an embodiment of the present technology. FIG. 5 illustrates the component parts of the example lens array 56 positioned in relation to other components of the assembly 12 including parts of the speculum 58 and the smartphone 10. The below described lenses are optically aligned along center axes thereof, and further optically aligned with the openings, thereby permitting the continuous path 22 for light, as shown and described herein. Table 1 specifies dimensions and additional details and values of the assembly of Example 1, where the feature numbers shown in parentheses in the below table correspond to those features shown in FIG. 5.

TABLE 1

Parameters of otoscope attachment assembly 12

| Designation | Designation Notes | Value(s) | Additional Information |
|---|---|---|---|
| $Distance_1$ (79) | Length between lens 1 (L1 (82)) and lens 4 (L4 (80)) | 20 mm | Lenses in between are all in contact with one another |
| $Distance_2$ (88) | Length between L4 (80) and lens 5 (L5 (90)) | 6.2 mm | |
| $Distance_3$ (92) | Length between L5 (90)) and the otoscope speculum opening (78) | 17 mm | The otoscope speculum opening (78) aperture diameter ranges from 4 mm (adults) to 2 mm (pediatrics) |
| $Distance_4$ (96) | Average distance between the otoscope speculum opening (78) and surface (98) of the tympanic membrane | 13-16 mm | 15 is the average for adults and about 13 for children (ages 6-12) |
| SRC (100) | Spherical Radius of Curvature | 2.5 mm | The SRCs 100 and Diameters of ball lenses L1 (82), L2 (80), L3 (84) and L4 (80) are all identical |
| $Dia_2$ (102) | Diameter of sphere | 5 mm | |
| L1 (82) L4 (80) | These lenses are identical and are made of BK7 glass (sometimes referred to as N-BK7 or in China and other countries it may be referred to as K9) | BK7 (nd = 1.517; Vd = 64.17) | Nd is the index of refraction of the glass. Vd is the dispersion index or Abbe Number of the glass. Other glass having the same or similar nd and Vd values can |
| L2 (86) L3 (84) | These lenses are identical and are made of optically clear sapphire. It is very scratch resistant and can be cut very thinly. It can be the same or similar to the material phone manufactures use to protect the camera (16) lens on the back of smartphones. | Sapphire (nd = 1.768; Vd = 72.31) | be substituted for BK7 or sapphire. |
| L5 (90) | This lens is made from N-Sf4 and is glued directly to the back of lens 6 (L6 (104)) with special optically transparent glue | N-Sf4 (nd = 1.755; Vd = 27.38) | This is an achromatic lens. It is used to correct chromatic aberrations in lens arrays. |
| L6 (104) | Same material as L1 (82) and L4 (80) | BK7 (nd = 1.517; Vd = 64.17) | Lenses (e.g., L5 (90) and L6 (104)) other than ball lenses L1 (82), L2 (86), L3 (84) and L4 (80) are also referred to herein as "non-ball lenses." Non-ball lens(es) are positioned distally relative the non-ball lens(es). |
| R1 ($Radius_1$ (106)) R2 ($Radius_2$ (108)) | This is the radius of curvature for the lens. R1 (106) = R2 (108). In addition, R2 (108) is shared between the touching surfaces of L5 (90) and L6 (104). | 4.0 mm | Technically, R2 is −4.0 mm since its curvature faces the opposite direction of the lens array direction (110). However, its value is functionally the same. |
| R3 ($Radius_3$ (112)) | R3 (112) faces L4 (80) | 19.0 mm | Again, technically this should be −19.00 mm |
| Effective Focal Length (EFL (114)) | The focal length of the achromatic lens set (116) using a wavelength of 586.6 nm | 9.01 mm | |
| Dia. (118) | Diameter of L5 (90) and L6 (104) | 3.0 mm | |
| BFL (120), ET (122), P (124), P" (126) | — | — | Not important |
| Aperture 1 (132) | The small opening only allows focused light (136) | 0.2-0.6 mm dia. | Aperture 2 (134) is located exactly at the EFL (114) of L5 |

TABLE 1-continued

Parameters of otoscope attachment assembly 12

| Designation | Designation Notes | Value(s) | Additional Information |
|---|---|---|---|
| Aperture 2 (134) | from the desired object (e.g., 98) to get through to the smartphone camera (16) and acts as a literal shield for all other stray light photons. Without it, the image would be blurry and would have a poor depth of field. | | (90)/L6 (104) lens set (116), whereas Aperture 1 (132) can be located anywhere between L1 (82) and the lens cover of the smartphone camera (16). Aperture 1 (132) prevents the image from appearing blurry as a digital image from the smartphone camera (16) and improves its depth of field (DOF). Aperture 1 (132) could be excluded if Aperture 2 (134) was sufficiently small and correctly placed, but due to inherent errors in manufacturing, this would be very difficult without a very precise piece of machinery. Combining the two apertures with slightly larger openings gets the job done equally well and cheaper. |

EXAMPLE 2

Figure 6:
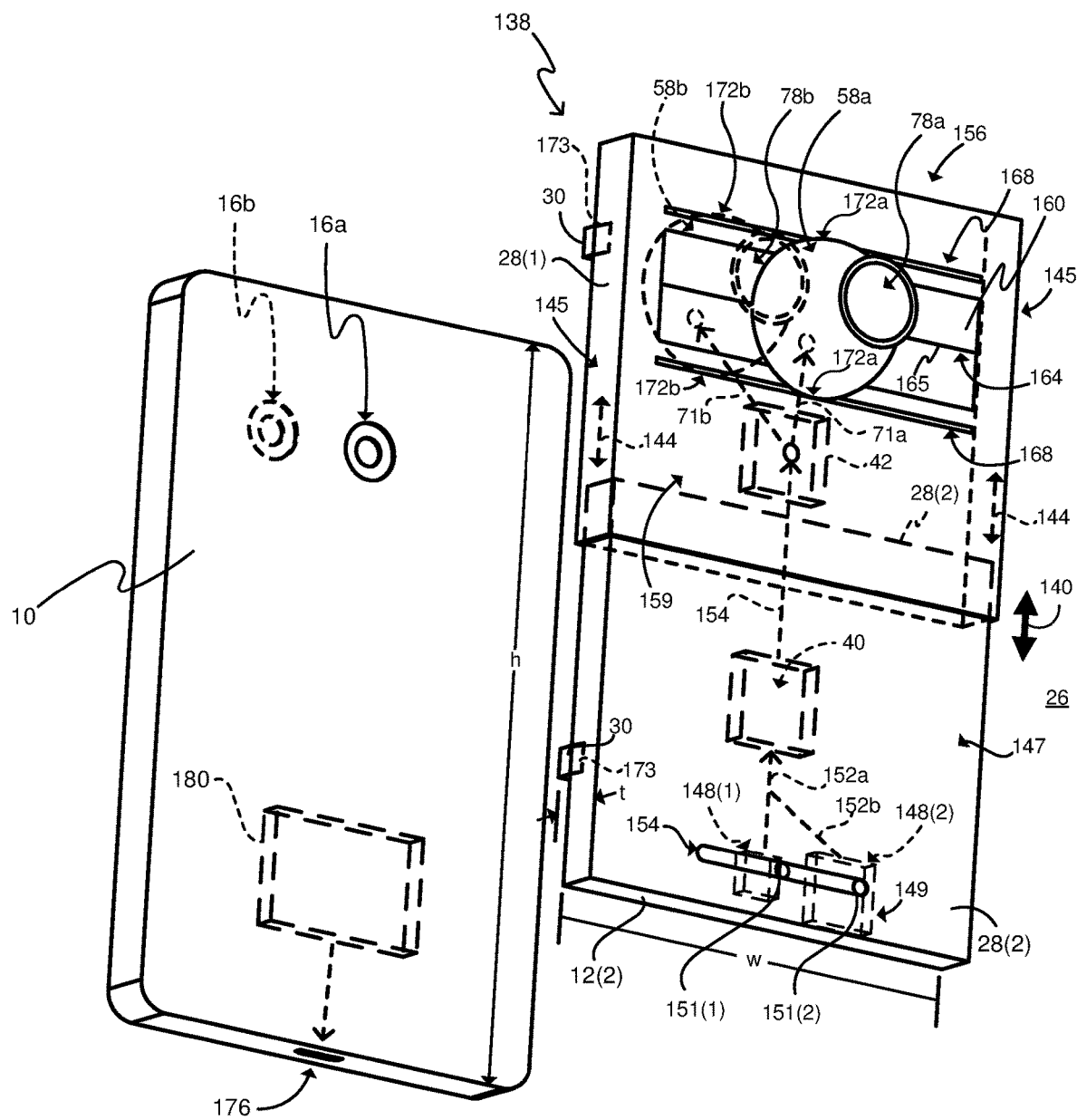
FIG. 6 depicts a perspective view of a smartphone otoscope attachment assembly, according to an embodiment of the present technology.

The technical benefits and advantages relating to the aforementioned universality of fit of the present technology can be achieved by way of mechanical design. In particular, the smartphone otoscope attachments of the present technology can have adjustable dimensions to enable them to fit smartphones having varying heights, widths and thicknesses. FIG. 6 depicts a perspective view of a smartphone otoscope attachment assembly 138, according to an embodiment of the present technology. Assembly 138 can include any of the features of mobile imaging device attachment 12 and assembly 101, as shown and described above with reference to FIGS. 1A-1C, 2A-2O, 3A-3G and 4 and as such FIG. 6 shares some of the same feature numbers as FIGS. 1A-1C and, 2A-2O, 3A-3G and 4.

Assembly 138 can include a means for adjusting the height of assembly 138. For example, and without limitation, assembly 138 can include body 28 formed as a two-piece body 28 that is shaped and dimensions to enable the height of assembly 138 to be adjusted to fit varying smartphone 10 heights (denoted "h" in FIG. 6). A first body piece 28(1) can include opposing slots 144 formed longitudinally on or in interior portions of opposing side panels 145, where the slot-to-slot distance is denoted "w" in FIG. 6. A second body piece 28(2) can have a width of w and be slidably fitted into slots 144, as shown in FIG. 6, thereby forming the two-piece body 28 and enabling user 48 to adjust the height of assembly 138 according to the smartphone 10 height h.

User 48 can slide piece 28(2) up or down (e.g., longitudinally) in the directions 140 shown in FIG. 6 until the desired height of the two-piece body 12 is thereby attained. This sliding action by user 48 can be accomplished either with the assembly 138 detached from, or attached to, smartphone 10. Additionally, or instead, the two-piece body 12 construction and the sliding action by user 48 can facilitate adjustment of the height of the assembly 138 to match the position of smartphone 10 imaging device 16 (e.g., a center of the exterior lens thereof) to the speculum 58 opening 78 to ensure that digital images obtained in use of assembly are clear of any obstructions. In some embodiments, power supply 40 or other electronic components 18 are electrically coupled to light source 42 by way of flexible or telescoping wire(s) or connector(s) 154 to facilitate retention of their functional and structural integrity upon being moved with the aforementioned sliding action by user 48. In addition to, or instead of, having the means for adjusting the height, assembly 138 can include a means for adjusting the width w of assembly 138. In an example, not shown in FIG. 6, the two-piece body 28 can be designed with slots for adjusting the width w of the assembly 138 an analogous manner as described above with respect to adjusting the height of assembly 138.

Assembly 138 can include a means for adjusting a lateral position of head 52 and speculum 58 of assembly 138. For example, and without limitation, assembly 138 can include a lateral sliding subsystem 156 formed in or on a portion of body 28 (e.g., on piece 28(1)). Material can be removed from, and through a material of construction of, a back-facing panel 159 of first body piece 28(1), thereby forming a window 164. Into window 164 may be fitted a two-piece gasket 160 having a lateral slot 165 permitting gasket 160 to be selectively and partially separated. Window 164 can span a portion of the width w, with a first portion of panel 159 remaining as is laterally above window 164, and the remainder of panel remaining as is laterally below window 164. One or more lateral slots 168 (two shown in FIG. 6) can be formed in exterior 26 facing portions of panel 159 (e.g., laterally above and below window 164). Head 52 (not shown for clarity) with speculum 58 attached can be fitted into slot 165, as shown in FIG. 6. Speculum 58 can have at least one extension 172 sized and dimensioned such that they can be slidably or removably fitted into the slot(s) 168.

The sliding attachment of head 52 and speculum 58 to body 28 enables user 48 to adjust the lateral positioning of opening 78 according to the corresponding position of imaging device 16 on smartphone 10. For instance, a first smartphone 10 model can have imaging device 16 with its lens in a first position 16*a*, and assembly 138 can be used with speculum 58, extension(s) 172 and opening 78 in respective positions 58*a*, 172*a* and 78*a*. For a second smartphone 10 model having imaging device 16 with its lens in a second position 16*b*, the same assembly 138 can be employed by the user 48 laterally sliding speculum 58, extension(s) 172 and its opening 78 to respective positions 58*b*, 172*b* and 78*b*. In some embodiments, light-redirecting element 71 is formed, at least in part, of a flexible material of construction to facilitate being optically coupled to light source 42 and retaining its full function upon being moved between, for instance, first 71*a* and second 71*b* positions.

Assembly 138 can include a means for adjusting the thickness (denoted t) of assembly 138. For example, and without limitation, assembly 138 can include slots 173 formed on or in interior portions of the opposing side panels 145, where the slots 173 are perpendicular to the back surface of assembly 138 body 28, as shown in FIG. 6. Clips 30 can be slidably inserted into slots 173, thereby permitting user 48 to move clips 30 into or out of the slots 173 to accommodate varying smartphone 10 thicknesses.

In addition to, or instead of, assembly 138 including the dimensional adjustment features described above by way of example, assembly 138 can include a means for selecting a smartphone 10 connector 148 from at least two such connectors 148. Different smartphone 10 models can include different ports 176 requiring particular connectors 148 to accomplish, for instance, charging of a smartphone 10 battery cell 180, data transfer, or for providing electric power to other devices from the smartphone 10. For example, and without limitation, the iPhone requires a unique connector (e.g., USB-C, or Lightning, connector 148(1)) for its port 176, where a connector (e.g., micro-USB connector 148(2)) for an Android-based smartphone 10 cannot be used to charge an iPhone.

In some embodiments, the means for selecting a smartphone 10 connector 148 can be embodied in, for example and without limitation, a connector selection subsystem 149 formed in or on a portion of body 28 (e.g., on piece 28(2)). Material can be removed from, and through a material of construction of, a back-facing panel 147 of second body piece 28(2), thereby forming a slot 154. At least two different connectors (e.g., 148(1) and 148(2)) can include one or more extensions (e.g., 151(1) and 151(2)) coupled to portions thereof, where the extensions are fitted into, and slidably coupled to and through, slot 154 to permit user 48 to manipulate (e.g., laterally slide) extensions 151 from the exterior 26 of assembly 138.

Each connector 148 can be electrically coupled to power supply 40 or electronic components 18 by way of flexible wire(s) or connector(s) 152 to facilitate retention of their functional and structural integrity upon being moved with the aforementioned sliding action by user 48. In the example shown in FIG. 6, smartphone 10 is an iPhone and its port 176 only accepts Lightning-type connector 148(1). For this case, user 48 can manipulate subsystem 149 by sliding it, along with wire 152, to the position corresponding to connector 148(1), with wire 152 in its respective position 152*a*. On the other hand, where smartphone 10 is an Android-type device having a micro-USB port 176, the same assembly 138 having subsystem 149 may be used. In this alternative case, user 48 can manipulate subsystem 149 by sliding it, along with wire 152, to the position corresponding to connector 148(2), with wire 152 in its respective position 152*b*. In some embodiments, slot 154 is laterally long enough to provide user 48 the option to not use either connector 148 in cases such as when power supply 40 does not require charging via the battery cell 180 of smartphone 10. In other embodiments, assembly 138 does not include power supply 40, and the smartphone 10 port 176 is always used to provide electric power to light source 42.

In operation, user 48 provides a smartphone 10 for use with assembly 138 and manipulates one or more of the aforementioned dimensional adjustment features to ensure proper fitting of assembly 138 according to the smartphone 10 size and shape, as well as imaging device 16 position. Where power supply 40 requires charging power, or for assembly 138 embodiments not having power supply 40, user 48 can determine which of a plurality of connectors 148 is compatible with port 176 and manipulates subsystem 149 accordingly, as described above. To facilitate a mating coupling of connector 148 to port 176, user can extend the height of assembly 138 to an extent that is greater (e.g., by just over the longitudinal length of connector 148) than the height h of smartphone 10. User 48 can then attach assembly 138 to smartphone 10 by way of clips 30, and then shorten the height of assembly 138 by the above described sliding action upwardly, thereby inserting connector 148 into port 176. At least a portion of second body piece 28(2) may be formed of an optically transparent material of construction to facilitate user 48 seeing the connector 148 and port 176 to ease alignment thereof for making the connection. With the smartphone 10 powered on, electric power may flow from battery cell 180 to either or both of power supply 40 and light source 42. The assembly 138 is thereby prepared for use in the above-described examination and diagnostic procedures.

Figure 7:
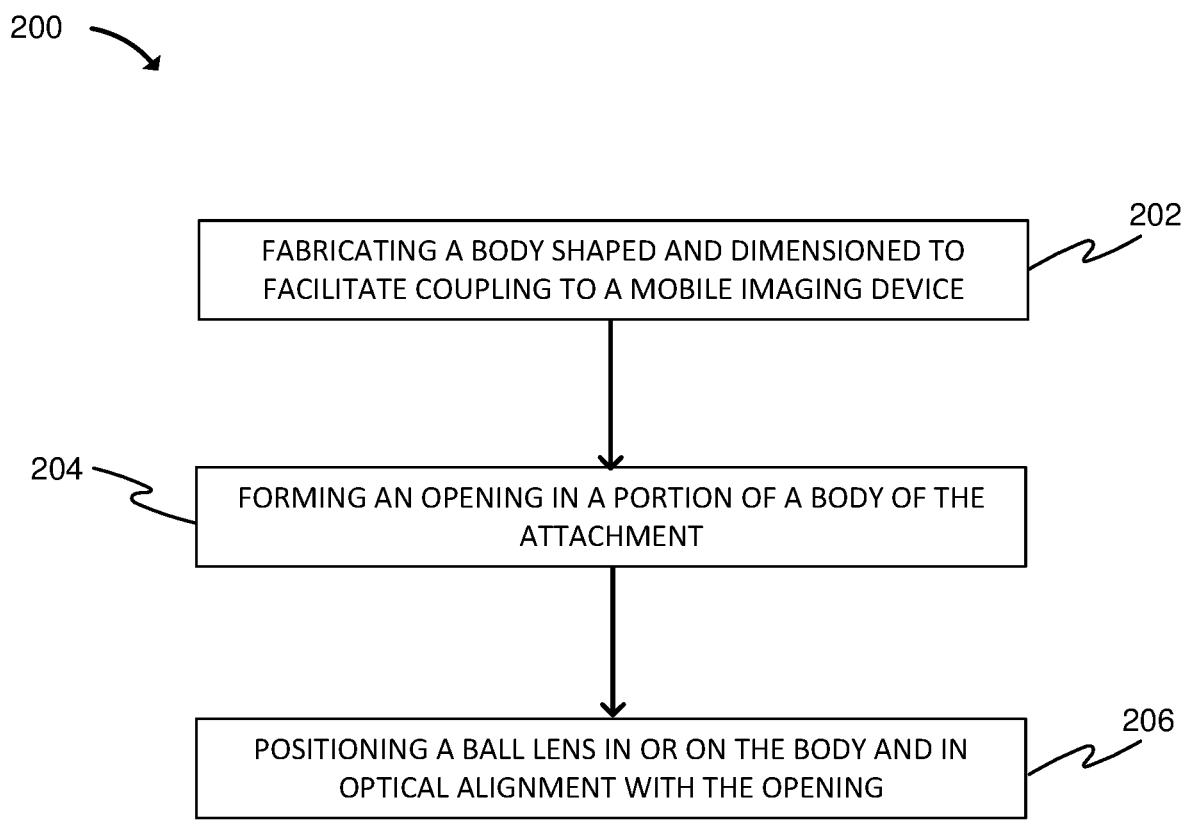
FIG. 7 is a flow chart of a method of manufacturing an attachment assembly, according to an embodiment of the present technology.

FIG. 7 is a flow chart of a method 200 of manufacturing an attachment assembly, according to an embodiment of the present technology. Method 200 includes fabricating 202 a body shaped and dimensioned to facilitate coupling to a mobile imaging device, such as a smartphone. Method 200 includes forming 204 an opening in a portion of the body of the attachment assembly. The forming 204 can be performed separately from (e.g., after), or concurrently with, the fabricating 202 step in method 200. Method 200 includes positioning 206 a ball lens in or on the body and in optical alignment with the opening. Method 200 can further include additional fabricating, forming and coupling steps to incorporate any or all of the above-described features of the present technology.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may thus be implemented using a variety of programming languages.

In alternative embodiments, the machine operates as a standalone device or may be connected (e.g., networked) to other machines. In a networked deployment, the machine may operate in the capacity of a server or a client machine in a client-server network environment or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above detailed description of embodiments of the disclosure is not intended to be exhaustive or to limit the teachings to the precise form disclosed above. While specific embodiments of, and examples for, the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are, at times, shown as being performed in a series, these processes or blocks may instead be performed in parallel, or may be performed at different times. Further, any specific numbers noted herein are only examples: alternative implementations may employ differing values or ranges.

The teachings of the disclosure provided herein can be applied to other systems, not necessarily the system described above. The elements and acts of the various embodiments described above can be combined to provide further embodiments.

Any patents and applications and other references noted herein, including any that may be listed in accompanying filing papers, are incorporated herein by reference. As to aspects of the disclosure can be modified, if necessary, to employ the systems, functions, and concepts of the various references described above to provide yet further embodiments of the disclosure.

These and other changes can be made to the disclosure in light of the above Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112(f), other aspects may likewise be embodied as a means-plus-function claim, or in other forms, such as being embodied in a computer-readable medium. (Any claims intended to be treated under 35 U.S.C. § 112(f) will begin with the words "means for".) Accordingly, the applicant reserves the right to add additional claims after filing the application to pursue such additional claim forms for other aspects of the disclosure.

The detailed description provided herein may be applied to other devices and systems, not necessarily only the devices and systems described above. The elements and acts of the various examples described above can be combined to provide further implementations of the invention. Some alternative implementations of the invention may include not only additional elements to those implementations noted above, but also may include fewer elements. These and other changes can be made to the invention in light of the above Detailed Description. While the above description defines certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention.

What is claimed is:

1. A mobile imaging device attachment, comprising:
   a body having an opening; and
   a ball lens having a diameter of from 2.5 mm to 7.5 mm positioned on or in the body and optically aligned with the opening,
   wherein the body is configured for coupling to a mobile imaging device with the opening optically aligned with a camera lens of the mobile imaging device.

2. The mobile imaging device attachment of claim 1, wherein the mobile imaging device attachment is an otoscope attachment.

3. The mobile imaging device attachment of claim 1 further comprising a light source.

4. The mobile imaging device attachment of claim 3 further comprising means for directing light from the light source toward the opening to illuminate an object positioned in an exterior of the body.

5. The mobile imaging device attachment of claim 1 further comprising a power source.

6. The mobile imaging device attachment of claim 1 further comprising at least two optically aligned ball lenses.

7. The mobile imaging device attachment of claim 1 further comprising at least three optically aligned ball lenses.

8. The mobile imaging device attachment of claim 1 further comprising means for attaching the body to a mobile device.

9. The mobile imaging device attachment of claim 8, wherein the mobile device is a smartphone.

10. The mobile imaging device attachment of claim 1 comprising at least two ball lenses, wherein at least one of the ball lenses is made of BK7 glass and at least one of the ball lenses is made of sapphire.

11. The mobile imaging device attachment of claim 1 further comprising a non-ball lens positioned on or in the body and optically aligned with the ball lens.

12. The mobile imaging device attachment of claim 11, wherein the non-ball lens is further positioned between the opening and the ball lens.

13. An assembly comprising:
    a body having an opening;
    a ball lens having a diameter of from 2.5 mm to 7.5 mm positioned on or in the body; and
    means for attaching the body to a mobile device to facilitate optically aligning an imaging device of the mobile device with the ball lens and the opening.

14. The assembly of claim 13, wherein the means for attaching includes one or more magnets.

15. The assembly of claim 13, wherein the mobile device is a smartphone.

16. The assembly of claim 13, wherein the means for attaching is an otoscope attachment.

17. The assembly of claim 13 further comprising a speculum optically aligned with the ball lens.

18. The assembly of claim 13 wherein the ball lens is made of BK7 glass or sapphire.

19. A method of manufacturing an attachment assembly, comprising:
    fabricating a body shaped and dimensioned to facilitate coupling to a mobile imaging device;
    forming an opening in a portion of the body of the attachment assembly; and
    positioning a ball lens having a diameter of from 2.5 mm to 7.5 mm in or on the body and in optical alignment with the opening.

20. The method of claim 19, wherein the body is further shaped and dimensioned to form an otoscope attachment.

* * * * *

UNITED STATES PATENT AND TRADEMARK OFFICE
CERTIFICATE OF CORRECTION

PATENT NO. : 11,241,149 B2  
APPLICATION NO. : 16/892358  
DATED : February 8, 2022  
INVENTOR(S) : Darren D. Lynn Page 1 of 1

It is certified that error appears in the above-identified patent and that said Letters Patent is hereby corrected as shown below:

On the Title Page

Item (71), Applicant, delete "The Regents of the University of Colorado" and insert --The Regents of the University of Colorado, a body corporate--

Item (73), Assignee, delete "The Regents of the University of Colorado" and insert --The Regents of the University of Colorado, a body corporate--

Signed and Sealed this  
Eighth Day of November, 2022

Katherine Kelly Vidal  
*Director of the United States Patent and Trademark Office*